(12) United States Patent
Kheradvar et al.

(10) Patent No.: US 12,734,034 B2
(45) Date of Patent: Sep. 15, 2026

(54) PERCUTANEOUS HEART VALVE DELIVERY SYSTEMS

(71) Applicant: THE REGENTS OF THE UNIVERSITY OF CALIFORNIA, Oakland, CA (US)

(72) Inventors: Arash Kheradvar, Irvine, CA (US); Jimmy L. Su, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1033 days.

(21) Appl. No.: 17/830,012

(22) Filed: Jun. 1, 2022

(65) Prior Publication Data

US 2022/0296369 A1 Sep. 22, 2022

Related U.S. Application Data

(63) Continuation-in-part of application No. 14/221,194, filed on Mar. 20, 2014, now abandoned, which is a (Continued)

(51) Int. Cl.
*A61F 2/24* (2006.01)
*A61B 8/08* (2006.01)
(Continued)

(52) U.S. Cl.
CPC .......... *A61F 2/2439* (2013.01); *A61B 8/0841* (2013.01); *A61B 8/0891* (2013.01);
(Continued)

(58) Field of Classification Search
CPC ...... A61F 2/2427; A61F 2/243; A61F 2/2433; A61F 2/2436; A61B 2019/5263;
(Continued)

(56) References Cited

U.S. PATENT DOCUMENTS 5,702,343 A 12/1997 Alferness
5,800,528 A 9/1998 Lederman et al.
(Continued)

FOREIGN PATENT DOCUMENTS

WO 2013/059747 A1 4/2013
WO 2020/168081 A1 8/2020
WO 2020236750 A1 11/2020

OTHER PUBLICATIONS

Cantwell et al. “Techniques for automated local activation time annotation and conduction velocity estimation in cardiac mapping.” Computers in biology and medicine 65 (2015): 229-242.
(Continued)

*Primary Examiner* — Anh T Dang
(74) *Attorney, Agent, or Firm* — NGUYEN TARBET IP LAW

(57) ABSTRACT

Embodiments described herein address the need for improved catheter devices for delivery, repositioning and/or percutaneous retrieval of the percutaneously implanted heart valves. One embodiment employs a plurality of spring-loaded arms releasably engaged with a stent frame for controlling expansion for valve deployment. Another embodiment employs a plurality of filaments passing through a distal end of a pusher sleeve and apertures in a self-expandable stent frame to control its state of deployment. With additional features, lateral positioning of the stent frame may also be controlled. Yet another embodiment includes plurality of outwardly biased arms held to complimentary stent frame features by overlying sheath segments. Still another embodiment integrates a visualization system in the subject delivery system. Variations on hardware and methods associated with the use of these embodiments are contemplated in addition to those shown and described.

5 Claims, 15 Drawing Sheets

Related U.S. Application Data continuation of application No. 13/862,302, filed on Apr. 12, 2013, now Pat. No. 9,668,859, and a continuation-in-part of application No. PCT/US2012/049645, filed on Aug. 3, 2012.

(60) Provisional application No. 61/732,117, filed on Nov. 30, 2012, provisional application No. 61/682,663, filed on Aug. 13, 2012, provisional application No. 61/666,657, filed on Jun. 29, 2012, provisional application No. 61/623,410, filed on Apr. 12, 2012, provisional application No. 61/515,679, filed on Aug. 5, 2011.

(51) Int. Cl.
*A61B 8/12* (2006.01)
*A61B 90/00* (2016.01)

(52) U.S. Cl.
CPC ................ *A61B 8/12* (2013.01); *A61B 90/37* (2016.02); *A61F 2/2427* (2013.01); *A61B 2090/3782* (2016.02)

(58) Field of Classification Search
CPC .... A61B 2019/5276; A61B 2019/5278; A61B 19/5225
See application file for complete search history.

(56) References Cited

U.S. PATENT DOCUMENTS 5,879,375 A 3/1999 Larson, Jr. et al.
6,309,379 B1 10/2001 Willard et al.
6,482,146 B1 11/2002 Alferness et al.
6,984,201 B2 1/2006 Khaghani et al.
7,491,170 B2 2/2009 Gharib
7,524,298 B2 4/2009 Gharib et al.
7,749,152 B2 7/2010 Gharib et al.
7,883,325 B2 2/2011 Kheradvar et al.
8,075,471 B2 12/2011 Trumble
8,133,270 B2 3/2012 Kheradvar et al.
8,794,937 B2 8/2014 Kheradvar et al.
9,370,425 B2 6/2016 Hjelle et al.
9,656,009 B2 5/2017 Kheradvar et al.
10,835,713 B2 11/2020 Homsy et al.
11,413,144 B2 8/2022 Rothstein et al.
2001/0041850 A1 11/2001 Brenneman et al.
2001/0047122 A1 11/2001 Vanden Hoek et al.
2002/0045799 A1 4/2002 Lau et al.
2005/0137682 A1 6/2005 Justino
2005/0240200 A1 10/2005 Bergheim
2005/0278010 A1 12/2005 Richardson
2006/0020377 A1 1/2006 Goetz et al.
2006/0043191 A1 3/2006 Patel et al.
2006/0167334 A1 7/2006 Anstadt et al.
2006/0259137 A1* 11/2006 Artof ...................... A61F 2/243 623/2.11
2007/0005131 A1 1/2007 Taylor
2007/0015958 A1 1/2007 Lau et al.
2007/0021826 A1 1/2007 Case et al.
2007/0038291 A1 2/2007 Case et al.
2007/0185369 A1 8/2007 Mirhoseini et al.
2007/0197859 A1 8/2007 Schaer et al.
2007/0203560 A1 8/2007 Forster et al.
2007/0208215 A1 9/2007 Hjelle et al.
2007/0239254 A1 10/2007 Chia et al.
2008/0046016 A1 2/2008 Ben-David et al.
2008/0228266 A1 9/2008 McNamara et al.
2009/0036730 A1 2/2009 Criscione et al.
2009/0131740 A1 5/2009 Gharib
2009/0264989 A1 10/2009 Bonhoeffer et al.
2009/0281619 A1 11/2009 Le et al.
2011/0019886 A1 1/2011 Mizuno
2011/0144690 A1 6/2011 Bishop et al.
2012/0165916 A1 6/2012 Jordan
2012/0283820 A1 11/2012 Tseng et al.
2013/0030519 A1 1/2013 Tran et al.
2013/0046377 A1 2/2013 Cohn
2013/0110895 A1 5/2013 Valentino et al.
2013/0243288 A1 9/2013 Goto
2013/0310923 A1 11/2013 Kheradvar et al.
2014/0107768 A1 4/2014 Venkatsubramanian
2014/0228943 A1 8/2014 Stigall et al.
2014/0316518 A1 10/2014 Kheradvar et al.
2014/0336743 A1 11/2014 Zotz
2014/0350350 A1 11/2014 Imagawa et al.
2015/0057488 A1 2/2015 Yomtov
2016/0045316 A1 2/2016 Braido et al.
2016/0206798 A1 7/2016 Williams et al.
2017/0080137 A1 3/2017 Criscione et al.
2017/0086974 A1 3/2017 Lashinski et al.
2017/0296055 A1 10/2017 Gardner et al.
2017/0319333 A1 11/2017 Tegels et al.
2018/0214266 A1 8/2018 Paul et al.
2018/0245243 A1 8/2018 Krieger et al.
2018/0300875 A1 10/2018 Imasugi
2019/0060542 A1 2/2019 Atlman et al.
2019/0133764 A1 5/2019 Carr et al.
2019/0282360 A1 9/2019 Colavito et al.
2019/0336280 A1 11/2019 Naor et al.
2020/0078002 A1 3/2020 Hacohen et al.
2020/0226422 A1 7/2020 Li et al.
2021/0275299 A1 9/2021 Peterson et al.
2022/0183830 A1 6/2022 Tseng et al.
2022/0233307 A1 7/2022 Tuval et al.

OTHER PUBLICATIONS

"Conventional Intracardiac Mapping Techniques"; https://thoracickey.com/conventional-intracardiac-mapping-techniques/; retrieved from web Jul. 1, 2024.

Clayton, Richard H., and Alexander V. Panfilov. "A guide to modelling cardiac electrical activity in anatomically detailed ventricles." Progress in biophysics and molecular biology 96.1-3 (2008): 19-43.

O'Shea et al. "ElectroMap: high-throughput open-source software for analysis and mapping of cardiac electrophysiology." Scientific reports 9.1 (2019): 1389.

Best, Kate E., and Judith Rankin. "Long-term survival of individuals born with congenital heart disease: a systematic review and meta-analysis." Journal of the American Heart Association 5.6 (2016): e002846.

Hoffman et al. "The incidence of congenital heart disease." Journal of the American college of cardiology 39.12 (2002): 1890-1900.

Dolk et al. "Congenital heart defects in Europe: prevalence and perinatal mortality, 2000 to 2005." Circulation 123.8 (2011): 841-849.

Oster, Matthew E., et al. "Temporal Trends in Survival Among Infants With Critical Congenital Heart Defects." Pediatrics 131.5 (2013): e1502-e1508.

Reller et al. "Prevalence of Congenital Heart Defects in Metropolitan Atlanta, 1998-2005." The Journal of pediatrics 153.6 (2008): 807.

Gilboa et al. "Congenital heart defects in the United States: estimating the magnitude of the affected population in 2010." Circulation 134.2 (2016): 101-109.

Liu et al. "Global birth prevalence of congenital heart defects 1970-2017: updated systematic review and meta- analysis of 260 studies." International journal of epidemiology 48.2 (2019): 455-463.

Davlouros et al. "The right ventricle in congenital heart disease." Heart 92 (2006): i27-i38.

Cho, Young Kuk, and Jae Sook Ma. "Right ventricular failure in congenital heart disease." Korean journal of pediatrics 56.3 (2013): 101.

Voelkel, et al. "Right ventricular function and failure: report of a National Heart, Lung, and Blood Institute working group on cellular and molecular mechanisms of right heart failure." Circulation 114.17 (2006): 1883-1891.

(56) References Cited

OTHER PUBLICATIONS

Haddad et al. "Right ventricular function in cardiovascular disease, part I: anatomy, physiology, aging, and functional assessment of the right ventricle." Circulation 117.11 (2008): 1436-1448.
Corno, Antonio F. "Pulmonary valve regurgitation: Neither interventional nor surgery fits all." Frontiers in Pediatrics 6 (2018): 169.
Martin et al. "Safety and feasibility of melody transcatheter pulmonary valve replacement in the native right ventricular outflow tract: a multicenter pediatric heart network scholar study." JACC: Cardiovascular Interventions 11.16 (2018): 1642-1650.
Zheng et al. "Long-term outcome of correction of tetralogy of Fallot in 56 adult patients." Chinese medical journal 126.19 (2013): 3675-3679.
Mitropoulos, et al. "Pulmonary valve replacement in patients with corrected tetralogy of Fallot." Journal of Cardiovascular and Thoracic Research 9.2 (2017): 71.
Warner et al. "Expanding the indications for pulmonary valve replacement after repair of tetralogy of Fallot." The Annals of thoracic surgery 76.4 (2003): 1066-1071.
Stern, Menachem, Matthew B. Pinson, and Arvind Murugan. "The complexity of folding self-folding origami." Physical Review X 7.4 (2017): 041070.
Peraza Hernandez, E. A., D. J. Hartl, and D. C. Lagoudas. "Design and simulation of origami structures with smooth folds." Proceedings of the Royal Society A: Mathematical, Physical and Engineering Sciences 473.2200 (2017): Jul. 16, 2016.
Schlickenrieder, Wolfram. "Nets of polyhedra." Master's Thesis, Technische Universität Berlin (1997).
Krankenberg et al. "Self-expanding versus balloon-expandable stents for iliac artery occlusive disease: the randomized ICE trial." JACC: Cardiovascular Interventions 10.16 (2017): 1694-1704.
Kheradvar et al. "Proof of concept of FOLDAVALVE, a novel 14 Fr totally repositionable and retrievable transcatheter aortic valve." EuroIntervention: journal of EuroPCR in collaboration with the Working Group on Interventional Cardiology of the European Society of Cardiology 11.5 (2015): 591-596.
Yi et al. "Bioinspired reversible hydrogel adhesives for wet and underwater surfaces." Journal of Materials Chemistry B 6.48 (2018): 8064-8070.
Zhao et al. "Bio-inspired reversible underwater adhesive." Nature communications 8.1 (2017): 1-8.
Lee, Haeshin, Bruce P. Lee, and Phillip B. Messersmith. "A reversible wet/dry adhesive inspired by mussels and geckos." Nature 448.7151 (2007): 338-341.
Cho et al. "Intrinsically reversible superglues via shape adaptation inspired by snail epiphragm." Proceedings of the National Academy of Sciences 116.28 (2019): 13774-13779.
Cools et al. "Medium term follow-up after percutaneous pulmonary valve replacement with the Melody® valve." IJC Heart & Vasculature 7 (2015): 92-97.
Zareian et al. "Effect of stent crimping on calcification of transcatheter aortic valves." Interactive cardiovascular and thoracic surgery 29.1 (2019): 64-73.
Lepidi et al. "Quantitative histological examination of bioprosthetic heart valves." Clinical infectious diseases 42.5 (2006): 590-596.
Lepidi et al. "Quantitative analysis of valvular lesions during Bartonella endocarditis." American journal of clinical pathology 114.6 (2000): 880-889.
Sellers et al. "Transcatheter aortic heart valves: histological analysis providing insight to leaflet thickening and structural valve degeneration." JACC: Cardiovascular Imaging 12.1 (2019): 135-145.
Martin, Caitlin, and Wei Sun. "Biomechanical characterization of aortic valve tissue in humans and common animal models." Journal of biomedical materials research. Part A 100.6 (2012).
Jiao et al. "Measurements of the Effects of Decellularization on Viscoelastic Properties of Tissues in Ovine, Baboon, and Human Heart Valves." Tissue Engineering. Part A 18.3-4 (2012): 423.
White et al. "Heart valve collagens: cross-species comparison using immunohistological methods." Journal of Heart Valve Disease 19.6 (2010): 766.
McCoy et al. "Sex-related differences in gene expression by porcine aortic valvular interstitial cells." PloS one 7.7 (2012): e39980.
Choo et al. "Development of an animal experimental model for a bileaflet mechanical heart valve prosthesis." Journal of Korean medical science 19.1 (2004): 37-41.
Capulli et al. "JetValve: Rapid manufacturing of biohybrid scaffolds for biomimetic heart valve replacement." Biomaterials 133 (2017): 229-241.
Ropcke et al. "Small intestinal submucosa tricuspid valve tube graft shows growth potential, remodelling and physiological valve function in a porcine model." Interactive CardioVascular and Thoracic Surgery 24.6 (2017): 918-924.
Yoon et al. "Outcomes of transcatheter mitral valve replacement for degenerated bioprostheses, failed annuloplasty rings, and mitral annular calcification." European heart journal 40.5 (2019): 441-451.
Guerrero et al. "1-year outcomes of transcatheter mitral valve replacement in patients with severe mitral annular calcification." Journal of the American College of Cardiology 71.17 (2018): 1841-1853.
Khan, Jaffar M., et al. "Anterior leaflet laceration to prevent ventricular outflow tract obstruction during transcatheter mitral valve replacement." Journal of the American College of Cardiology 73.20 (2019): 2521-2534.
Blanke et al. "Predicting LVOT obstruction in transcatheter mitral valve implantation: concept of the neo-LVOT." JACC: Cardiovascular Imaging 10.4 (2017): 482-485.
Khan et al. ""Rescue" LAMPOON to Treat Transcatheter Mitral Valve Replacement-Associated Left Ventricular Outflow Tract Obstruction." JACC: Cardiovascular Interventions 12.13 (2019): 1283-1284.
Khan et al. "LAMPOON to facilitate Tendyne transcatheter mitral valve replacement." JACC: Cardiovascular Interventions 11.19 (2018): 2014-2017.
Greenbaum et al. "Long or redundant leaflet complicating transcatheter mitral valve replacement: case vignettes that advocate for removal or reduction of the anterior mitral leaflet." Catheterization and Cardiovascular Interventions 92.3 (2018): 627-632.
USPTO, "Non-Final Office Action", issued in connection with U.S. Appl. No. 17/088,989, dated Apr. 11, 2025, 18 pages.
USPTO, "Non-Final Office Action", issued in connection with U.S. Appl. No. 17/680,636, dated Mar. 4, 2025, 16 pages.
Zegdi et al. "Evidence of leaflet injury during percutaneous aortic valve deployment." European journal of cardio-thoracic surgery 40.1 (2011): 257-260.
De Buhr et al. "Impairment of pericardial leaflet structure from balloon-expanded valved stents." The Journal of Thoracic and Cardiovascular Surgery 143.6 (2012): 1417-1421.
Ong, Sea Hing, Ralf Mueller, and Stein Iversen. "Early calcific degeneration of a CoreValve transcatheter aortic bioprosthesis." European heart journal 33.5 (2012): 586-586.
Harbaoui et al. "Early Edwards SAPIEN valve degeneration after transcatheter aortic valve replacement." JACC: Cardiovascular Interventions 9.2 (2016): 198-199.
Webb, John G., and Danny Dvir. "Is transcatheter aortic valve replacement a durable therapeutic strategy ?." JACC: Cardiovascular Interventions 8.8 (2015): 1092-1094.
Sinha, Aditi, Oleksandr Barannyk, and Arash Kheradvar. "Crimp induced leaflet damage and calcification of transcatheter heart valves." Cardiology 134.2 (2016): 170-171.
Makkar, Raj R., and Tarun Chakravarty. "Transcatheter aortic valve thrombosis: new problem, new insights." JACC: Cardiovascular Interventions 10.7 (2017): 698-700.
Bush, Charles H., John D. Reith, and Suzanne S. Spanier. "Mineralization in Musculoskeletal Leiomyosarcoma: Radiologic-Pathologic Correlation." American Journal of Roentgenology 180.1 (2003): 109-113.
Otto, C. M. "Calcification of bicuspid aortic valves." Heart 88.4 (2002): 321-322.
Alavi, S. Hamed, Elliott M. Groves, and Arash Kheradvar. "The effects of transcatheter valve crimping on pericardial leaflets." The Annals of thoracic surgery 97.4 (2014): 1260-1266.

(56) References Cited

OTHER PUBLICATIONS

Dasi, Lakshmi P., et al. "On the mechanics of transcatheter aortic valve replacement." Annals of biomedical engineering 45.2 (2017): 310-331.
Delogne, Christophe, et al. "Characterization of the calcification of cardiac valve bioprostheses by environmental scanning electron microscopy and vibrational spectroscopy." Journal of microscopy 228.1 (2007): 62-77.
Schoen, Frederick J., Jack W. Tsao, and Robert J. Levy. "Calcification of bovine pericardium used in cardiac valve pioprostheses. Implications for the mechanisms of bioprosthetic tissue mineralization." The American journal of pathology 123.1 (1986): 134.
Bertazzo et al. "Nano-analytical electron microscopy reveals fundamental insights into human cardiovascular tissue calcification." Nature materials 12.6 (2013): 576-583.
Schoen, Frederick J., and Robert J. Levy. "Calcification of tissue heart valve substitutes: progress toward understanding and prevention." The Annals of thoracic surgery 79.3 (2005): 1072-1080.
Khoffi et al. "Transcatheter fiber heart valve: effect of crimping on material performances." Journal of Biomedical Materials Research Part B: Applied Biomaterials 103.7 (2015): 1488-1497.
Arora et al. "Early transcatheter valve prosthesis degeneration and future ramifications." Cardiovascular Diagnosis and Therapy 7.1 (2017): 1.
Chhatriwalla et al. "Bioprosthetic valve fracture improves the hemodynamic results of valve-in-valve transcatheter aortic valve replacement." Circulation: Cardiovascular Interventions 10.7 (2017): e005216.
Sathananthan et al. "Valve-in-valve transcatheter aortic valve replacement and bioprosthetic valve fracture comparing different transcatheter heart valve designs: an ex vivo bench study." JACC: Cardiovascular Interventions 12.1 (2019): 65-75.
Yuan S-M, Mishaly D, Shinfeld A, Raanani E. Right ventricular outflow tract reconstruction: Valved conduit of choice and clinical outcomes. Journal of Cardiovascular Medicine. 2008;9:327-337.
Gatzoulis MA, Balaji S, Webber SA, Siu SC, Hokanson JS, Poile C, Rosenthal M, Nakazawa M, Moller JH, Gillette PC, Webb GD, Redington AN. Risk factors for arrhythmia and sudden cardiac death late after repair of tetralogy of fallot: A multicentre study. The Lancet. 2000;356:975-981.
Texakalidis P, Giannopoulos S, Kokkinidis DG, Lanzino G. Effect of open- vs closed-cell stent design on periprocedural outcomes and restenosis after carotid artery stenting: A systematic review and comprehensive meta-analysis. Journal of Endovascular Therapy. 2018;25:523-533.
Jalal Z, Galmiche L, Lebeaux D, Villemain O, Brugada G, Patel M, Ghigo J-M, Beloin C, Boudjemline Y. Selective propensity of bovine jugular vein material to bacterial adhesions: An in-vitro study. International Journal of Cardiology. 2015;198:201-205.
Richardt, Doreen, Thorsten Hanke, and Hans-Hinrich Sievers. "Two cases of heart failure after implantation of a CoreValve prosthesis." The New England journal of medicine 372.11 (2015): 1079-1080.
Thielmann, M., et al. "Current developments in transcatheter aortic valve implantation techniques." Herz 36.8 (2011): 696-705.
Svensson, Lars G., et al. "United States feasibility study of transcatheter insertion of a stented aortic valve by the left ventricular apex." The Annals of thoracic surgery 86.1 (2008): 46-55.
Pislaru SV, et al. 2014 Progress in Cardiovascular Diseases 57:32-46.
Bartel T, et al. 2011 Journal of the American Society of Echocardiography 24:966-975.
Okabe, Teruo, et al. "The predictive value of computed tomography calcium scores: a comparison with quantitative volumetric intravascular ultrasound." Cardiovascular Revascularization Medicine 10.1 (2009): 30-35.
Beebe, Hugh G. "Imaging modalities for aortic endografting." Journal of Endovascular Therapy 4.2 (1997): 111-123.
Kawase, Yoshiaki, et al. "In vivo volumetric analysis of coronary stent using optical coherence tomography with a novel balloon occlusion-flushing catheter: a comparison with intravascular ultrasound." Ultrasound in medicine & biology 31.10 (2005): 1343-1349.
Ávila, P., et al. "IVUS guidance in percutaneous closure of aortic paraprosthetic leak." Cardiovascular intervention and therapeutics 27.2 (2012): 137-139.
Alboliras, Ernerio T., and Ziyad M. Hijazi. "Comparison of costs of intracardiac echocardiography and transesophageal echocardiography in monitoring percutaneous device closure of atrial septal defect in children and adults." The American journal of cardiology 94.5 (2004): 690-692.
Falahatpisheh, Ahmad, and Arash Kheradvar. "High-speed particle image velocimetry to assess cardiac fluid dynamics in vitro: From performance to validation." European Journal of Mechanics-B/Fluids 35 (2012): 2-8.
Kiefer, Philipp, et al. "Crimping may affect the durability of transcatheter valves: an experimental analysis." The Annals of thoracic surgery 92.1 (2011): 155-160.
Van Steenberghe, Mathieu, et al. "Early transcatheter aortic valve degeneration in the young." International Journal of Cardiology 222 (2016): 786-787.
Pascual, Isaac, Pablo Avanzas, and Cesar Moris. "Degenerative pattern of a percutaneous aortic valve." Revista espanola de cardiologia (English ed.) 70.9 (2017): 772.
Kapolos et al. "Model experimental system for investigation of heart valve calcification in vitro." Journal of biomedical materials research 38.3 (1997): 183-190.
Krings et al. "Development of a new combined test setup for accelerated dynamic pH-controlled in vitro calcification of porcine heart valves." The International Journal of Artificial Organs 32.11 (2009): 794-801.
Tertti, Risto, et al. "Comparison of calcium phosphate product values using measurement of plasma total calcium and serum ionized calcium." Hemodialysis International 11.4 (2007): 411-416.
Cheng, Ching-Li, et al. "Ex vivo assessment of valve thickness/calcification of patients with calcific aortic stenosis in relation to in vivo clinical outcomes." Journal of the Mechanical Behavior of Biomedical Materials 74 (2017): 324-332.
Foroutan, Farid, et al. "Structural valve deterioration after transcatheter aortic valve implantation." Heart 103.23 (2017): 1899-1905.
Leon MB, et al. "Transcatheter aortic valve implantation for aortic stenosis in patients who cannot undergo surgery" 2010 The New England Journal of Medicine 363:1597-1607.
Mack, Michael J. "Does transcatheter aortic valve implantation mean the end of surgical aortic valve replacement?." Texas Heart Institute Journal 37.6 (2010): 658.
Cribier et al. "Percutaneous transcatheter implantation of an aortic valve prosthesis for calcific aortic stenosis: first human case description." Circulation 106.24 (2002): 3006-3008.
Makkar, et al. "Transcatheter aortic-valve replacement for inoperable severe aortic stenosis." New England Journal of Medicine 366.18 (2012): 1696-1704.
Geisbüsch et al. "Incidence and management of CoreValve dislocation during transcatheter aortic valve implantation." Circulation: Cardiovascular Interventions 3.6 (2010): 531-536.
Thomas et al. "Thirty-day results of the SAPIEN aortic Bioprosthesis European Outcome (SOURCE) Registry: a European registry of transcatheter aortic valve implantation using the Edwards SAPIEN valve." Circulation 122.1 (2010): 62-69.
Ussia, et al. "The valve-in-valve technique for treatment of aortic bioprosthesis malposition: an analysis of incidence and 1-year clinical outcomes from the Italian CoreValve registry." Journal of the American College of Cardiology 57.9 (2011): 1062-1068.
Masson et al. "Transcatheter aortic valve implantation: review of the nature, management, and avoidance of procedural complications." JACC: Cardiovascular Interventions 2.9 (2009): 811-820.
Webb, John G., et al. "Transcatheter valve-in-valve implantation for failed bioprosthetic heart valves." Circulation 121.16 (2010): 1848-1857.
Gurvitch et al. "Transcatheter valve-in-valve implantation for failed surgical bioprosthetic valves." Journal of the American College of Cardiology 58.21 (2011): 2196-2209.

(56) References Cited

OTHER PUBLICATIONS

Groves et al. "The effects of positioning of transcatheter aortic valve on fluid dynamics of the aortic root." ASAIO journal (American Society for Artificial Internal Organs: 1992) 60.5 (2014): 545.
Su, Jimmy Li-Shin, Bo Wang, and Stanislav Y. Emelianov. "Photoacoustic imaging of coronary artery stents." Optics Express 17.22 (2009): 19894-19901.
Elgort, et al. "Image-guided and-monitored renal artery stenting using only MRI." Journal of Magnetic Resonance Imaging: An Official Journal of the International Society for Magnetic Resonance in Medicine 23.5 (2006): 619-627.
De Heer et al. "Multimodality imaging throughout transcatheter aortic valve implantation." Future Cardiology 8.3 (2012): 413-424.
Jilaihawi et al. "Cross-sectional computed tomographic assessment improves accuracy of aortic annular sizing for transcatheter aortic valve replacement and reduces the incidence of paravalvular aortic regurgitation." Journal of the American College of Cardiology 59.14 (2012): 1275-1286.
Willson et al. "3-dimensional aortic annular assessment by multidetector computed tomography predicts moderate or severe paravalvular regurgitation after transcatheter aortic valve replacement: a multicenter retrospective analysis." Journal of the American College of Cardiology 59.14 (2012): 1287-1294.
Jilaihawi et al. "A revised methodology for aortic-valvar complex calcium quantification for transcatheter aortic valve implantation." Eur Heart J Cardiovasc Imaging. Dec. 2014; 15(12):1324-32.
White et al. "The role of cinefluoroscopy and intravascular ultrasonography in evaluating the deployment of experimental endovascular prostheses." Journal of vascular surgery 21.3 (1995): 365-374.
Moss et al. "Role of echocardiography in percutaneous aortic valve implantation." JACC: Cardiovascular Imaging 1.1 (2008): 15-24.
Naqvi, Tasneem Z. "Echocardiography in percutaneous valve therapy." JACC: Cardiovascular Imaging 2.10 (2009): 1226-1237.
Dumont et al. "Feasibility of transapical aortic valve implantation fully guided by transesophageal echocardiography." The Journal of Thoracic and Cardiovascular Surgery 138.4 (2009): 1022-1024.
Jánosi et al. "Guidance of percutaneous transcatheter aortic valve implantation by real-time three-dimensional transesophageal echocardiography—A single-center experience." Minimally Invasive Therapy & Allied Technologies 18.3 (2009): 142-148.
Bartel et al. "Intracardiac echocardiography for guidance of transcatheter aortic valve implantation under monitored sedation: a solution to a dilemma?." European Heart Journal-Cardiovascular Imaging 17.1 (2016): 1-8.
Sengupta et al. "Transthoracic echocardiography guidance for TAVR under monitored anesthesia care." Cardiovascular Imaging 8.3 (2015): 379-380.
Choi et al. "Relationship between coronary artery calcium score by multidetector computed tomography and plaque components by virtual histology intravascular ultrasound." Journal of Korean medical science 26.8 (2011): 1052-1060.
Kpodonu, Jacques, Venkatesh G. Ramaiah, and Edward B. Diethrich. "Intravascular ultrasound imaging as applied to the aorta: a new tool for the cardiovascular surgeon." The Annals of thoracic surgery 86.4 (2008): 1391-1398.
Mintz et al. "American College of Cardiology clinical expert consensus document on standards for acquisition, measurement and reporting of intravascular ultrasound studies (ivus) A report of the american college of cardiology task force on clinical expert consensus documents developed in collaboration with the european society of cardiology endorsed by the society of cardiac angiography and interventions." Journal of the American College of Cardiology 37.5, 1478-192. Elsevier; New York, NY, United States.
Ferrari et al. "Imaging for trans-catheter pulmonary stent-valve implantation without angiography: role of intravascular ultrasound." European journal of cardio-thoracic surgery 40.2 (2011): 522-524.
Mathur, S. K., and Pooja Singh. "Transoesophageal echocardiography related complications." Indian Journal of Anaesthesia 53.5 (2009): 567.
Jánosi et al. "Quantitative analysis of aortic valve stenosis and aortic root dimensions by three-dimensional echocardiography in patients scheduled for transcutaneous aortic valve implantation." Current cardiovascular imaging reports 7.11 (2014): 1-9.
Maragiannis, Dimitrios, and Stephen H. Little. "Interventional imaging: the role of echocardiography." Methodist DeBakey cardiovascular journal 10.3 (2014): 172.
Klein, Andrew A., Nikolas J. Skubas, and Joerg Ender. "Controversies and complications in the perioperative management of transcatheter aortic valve replacement." Anesthesia & Analgesia 119.4 (2014): 784-798.
Klein et al. "Economic analysis of a transesophageal echocardiography-guided approach to cardioversion of patients with atrial fibrillation: the ACUTE economic data at eight weeks." Journal of the American College of Cardiology 43.7 (2004): 1217-1224.
Roy et al. "First-in-man use of aortic valve ultrasound for assessment of aortic valve anatomy pre-and post-transcatheter aortic valve implantation." JACC: Cardiovascular Interventions 6.6 (2013): 634-635.
Kheradvar et al. "Emerging trends in heart valve engineering: Part IV. Computational modeling and experimental studies." Annals of biomedical engineering 43.10 (2015): 2314-2333.
Kahlert et al. "Towards real-time cardiovascular magnetic resonance guided transarterial CoreValve implantation: in vivo evaluation in swine." Journal of Cardiovascular Magnetic Resonance 14.1 (2012): 1-15.
Kapadia et al. "Imaging for transcatheter valve procedures." Current problems in cardiology 35.5 (2010): 228-276.
Kheradvar, Arash, and Morteza Gharib. "On mitral valve dynamics and its connection to early diastolic flow." Annals of biomedical engineering 37.1 (2009): 1-13.
Kheradvar et al. "An in vitro study of changing profile heights in mitral bioprostheses and their influence on flow." Asaio Journal 52.1 (2006): 34-38.
Kheradvar, Arash, Michele Milano, and Morteza Gharib. "Correlation between vortex ring formation and mitral annulus dynamics during ventricular rapid filling." Asaio Journal 53.1 (2007): 8-16.
Tsukui et al. "Cerebrovascular accidents in patients with a ventricular assist device." The Journal of thoracic and cardiovascular surgery 134.1 (2007): 114-123.
Kirklin et al. "Fifth INTERMACS annual report: risk factor analysis from more than 6,000 mechanical circulatory support patients." The Journal of heart and lung transplantation 32.2 (2013): 141-156.
Starling et al. "Unexpected abrupt increase in left ventricular assist device thrombosis." New England Journal of Medicine 370.1 (2014): 33-40.
Kirklin et al. "Interagency Registry for Mechanically Assisted Circulatory Support (INTERMACS) analysis of pump thrombosis in the HeartMate II left ventricular assist device." The Journal of Heart and Lung Transplantation 33.1 (2014): 12-22.
Rigatelli, Gianluca, Francesco Santini, and Giuseppe Faggian. "Past and present of cardiocirculatory assist devices: a comprehensive critical review." Journal of Geriatric Cardiology: JGC 9.4 (2012): 389.
Almond, Christopher S. "The FDA review process for cardiac medical devices in children: a review for the clinician." Progress in pediatric cardiology 33.2 (2012): 105-109.
Grosberg, Anna, Morteza Gharib, and Arash Kheradvar. "Effect of fiber geometry on pulsatile pumping and energy expenditure." Bulletin of mathematical biology 71.7 (2009): 1580-1598.
Leon et al. "Transcatheter or surgical aortic-valve replacement in intermediate-risk patients." New England Journal of Medicine 374.17 (2016): 1609-1620.
Dvir et al. "Standardized definition of structural valve degeneration for surgical and transcatheter bioprosthetic aortic valves." Circulation 137.4 (2018): 388-399.
Kheradvar, Arash, et al. "Emerging trends in heart valve engineering: Part II. Novel and standard technologies for aortic valve replacement." Annals of biomedical engineering 43.4 (2015): 844-857.

(56) References Cited

OTHER PUBLICATIONS

USPTO, "Non-Final Office Action", issued in connection with U.S. Appl. No. 18/170,341, dated Jun. 3, 2025, 12 pages.

* cited by examiner 122
120

122
120

110
100
20
122

140
120
110
120
110
112

110
114
118
116
112
120

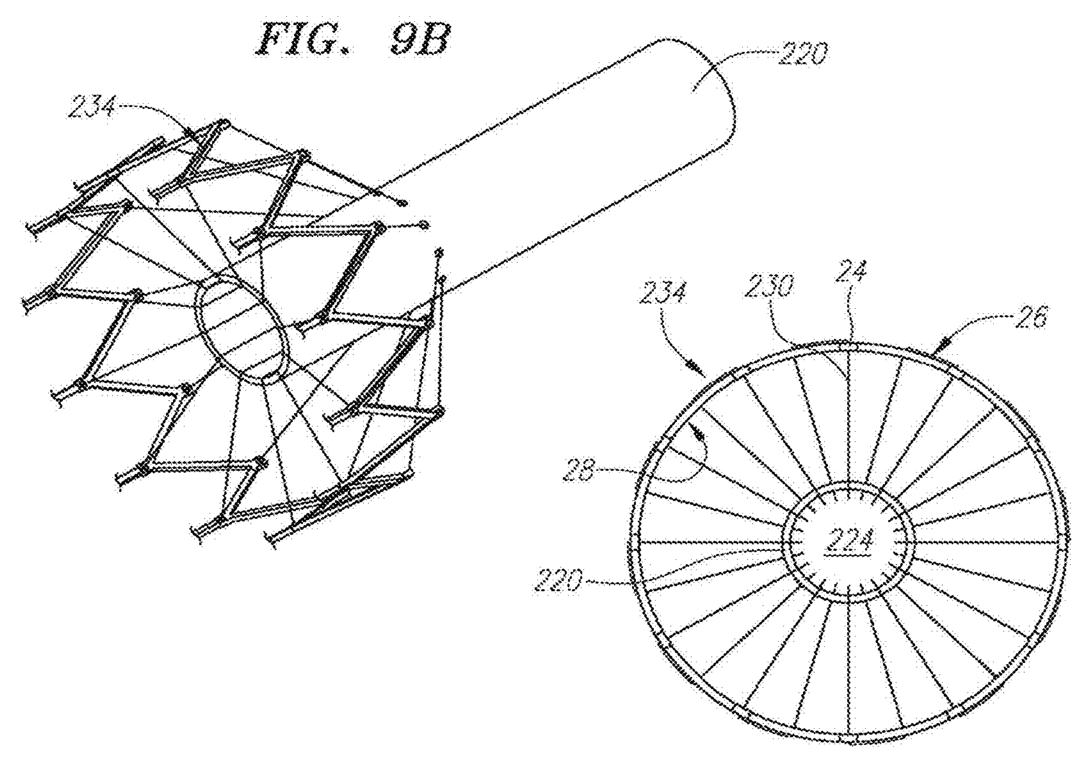
FIG. 9B
FIG. 9C
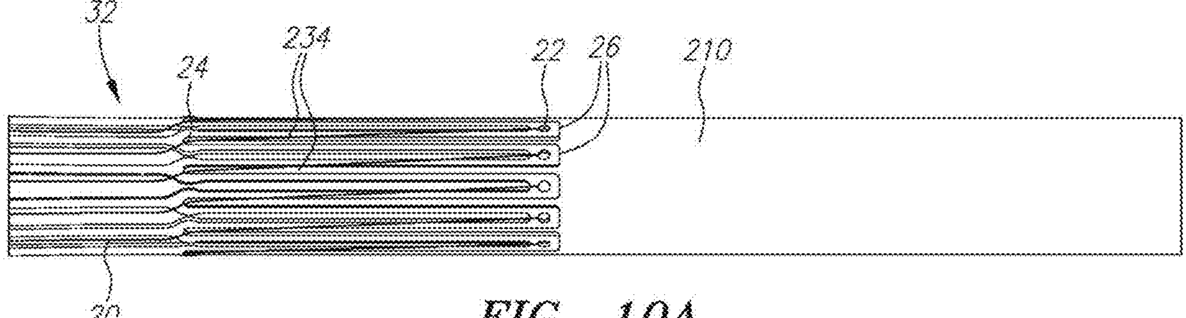
FIG. 10A
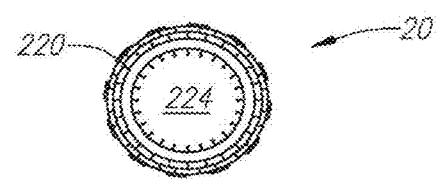
FIG. 10B 20
200'
220
A
A
B
B
252
250
230

12
1
11
2
10
3
9
4
8
5
7
6
A-A
B-B
20
200'
230
230
250
220
δl1
δl2
δl2
δl1

PERCUTANEOUS HEART VALVE DELIVERY SYSTEMS

CROSS-REFERENCES TO RELATED APPLICATIONS

This application is a continuation-in-part, and claims benefit of U.S. patent application Ser. No. 14/221,194 filed Mar. 20, 2014, which is a continuation of U.S. patent application Ser. No. 13/862,302, filed Apr. 12, 2013, which claims the benefit of and priority to U.S. Provisional Patent Application No. 61/732,117, filed Nov. 30, 2012, U.S. Provisional Patent Application No. 61/682,663, filed Aug. 13, 2012, and U.S. Provisional Patent Application No. 61/623,410, filed Apr. 12, 2012.

This application is also a continuation-in-part, and claims benefit of U.S. patent application Ser. No. 14/221,194 filed Mar. 20, 2014, which is a continuation-in-part of PCT/US12/49645, filed Aug. 3, 2012, which claims the benefit of and priority to U.S. Provisional Patent Application No. 61/515,679, filed Aug. 5, 2011, and U.S. Provisional Patent Application No. 61/666,657, filed Jun. 29, 2012. All preceding applications are incorporated by reference herein in their entireties for all purposes.

FIELD OF THE INVENTION

The embodiments described herein relate to percutaneously-delivered heart valves and associated delivery systems.

BACKGROUND OF THE INVENTION

Transcatheter aortic valve replacement (TAVR) procedures require image-guidance during implantation to successfully deploy the heart valve into the correct position within the patient's aortic annulus. Current image technology uses X-Ray, CT, MRI, or ultrasound to visualize the surrounding anatomy. However, only X-Ray can be used during the procedure for image guidance. X-Ray is not sufficient for visualization because it is a 2D projection of 3D anatomy that depends on the orientation angle of visualization. Currently, other imaging modalities can be used prior to the procedure and during follow-up, with the hopes that anatomical visualization can be directly correlated to the X-Ray images seen during the procedure. However, differences in contrast, resolution, and artifacts can produce differing results.

Correct valve positioning is crucial for treatment success and optimal outcomes after transcatheter valve implantation. For example, to maintain a stable and correct lengthwise position with respect to the aortic annulus, a stepwise deployment that allows the valve to be repositioned both circumferentially and in the axial direction (i.e., towards the left ventricle (LV) or the ascending aorta) is important.

However, most of the current technologies are limited by instant deployment, and once the valve is deployed, repositioning and/or percutaneous retrieval is not possible—or at least difficult or potentially problematic. Placement of the stented valve in a position that is too high (or proximal) can totally or partially obstruct the coronary ostia in a case of aortic implantation, which may result in myocardial infarction or ischemia. Additionally, if the valve is placed too high in the aorta, it may embolize into the aorta causing significant paravalvular regurgitation. On the other hand, implantation in a position that is too low (or distal) is accompanied by compression of the atrioventricular (AV) node in the membranous septum, which leads to conduction abnormalities.

Further technical developments with a focus on a positionable, repositionable, and/or percutaneously retrievable valve design allow optimal placement and may thereby significantly reduce the risk of paravalvular aortic regurgitation, myocardial infarction, or ischemia related to improper positioning. Likewise, advances in imaging to facilitate optimal heart valve placement are needed.

BRIEF SUMMARY OF THE INVENTION

The embodiments described herein address the need for improved catheter devices for coordinated delivery, positioning, repositioning and/or percutaneous retrieval of the percutaneously implanted heart valves. The delivery system apparatus is a tool that may incorporate a guide wire lumen. As such, a given device may be suitable for so-called "over-the-wire" use and include a delivery sheath covering that restrains the stent frame of the valve. Alternatively, the delivery device may be tracked through a catheter serving such function, as in a so-called "guide" or "delivery" catheter.

The present invention features a delivery system comprising an implantable heart valve, a valve delivery catheter comprising a first lumen, and an ultrasound imaging catheter inserted through the center of the first lumen of the valve delivery catheter (see FIG. 21A). The valve delivery catheter may be reversibly coupled with the implantable heart valve at a distal end of the valve delivery catheter. In some embodiments, the ultrasound imaging catheter comprises a guide wire lumen and an ultrasound imaging transducer located at a distal end of the ultrasound imaging catheter. The ultrasound imaging catheter may be configured to moveably pass: (i) over a guide wire passing through the guide wire lumen of the ultrasound imaging catheter, (ii) through the first lumen of the valve delivery catheter, and (iii) through the implantable heart valve.

In one embodiment, the delivery apparatus includes a number of arms (such as, but not limited to three) embedded within its body that hold the valve's stent during the delivery procedure when it is in the collapsed state. The arms are equipped with adjustable springs that are remotely controllable by the operator, and allow for robust radial expansion or deployment of the collapsed stent in increments.

In use, the arms remain attached to the valve stent frame until the stent frame is fully deployed. If the stent/stent frame is not properly deployed, the arms, which are still releasably attached to the stent until intended release, can be used for partial contraction of the stent for repositioning purposes. When the stented valve is properly positioned as desired within the heart, the arms will be released from the stent, and return to their embedded/retracted positions within the apparatus. Then the entire apparatus is retracted. It may be retracted from the heart or vasculature over any guide wire used and/or through any delivery catheter employed for site access.

In another system embodiment allowing for stented valve delivery, repositioning, and/or percutaneous retrieval, draw line filaments are positioned through the distal end of a pusher sleeve (or draw tube), along a lumen of the sleeve (or tube), out through holes in the sleeve (or tube), out through proximal frame holes, along the surface of a heart valve frame, in through distal frame holes, in through the distal end of the sleeve (or tube), along the lumen of the sleeve (or tube), and out the proximal end of the sleeve (or tube).

Variations on this approach are possible as are various optional features of the stent frame facilitating such use.

The draw lines may comprise polyester (PE), P1FE, suture material, or another high strength (and preferably biocompatible fiber) braid or bundle of fibers such as ultra-high-molecular-weight polyethylene (UHMWPE, sometimes shortened to UHMW). In this embodiment and others described herein, the heart valve frame may comprise superelastic NiTi alloy heatset in a desired shape, it may be constructed of a so-called "engineering plastic" such as polyetheretherketone (PEEK) or may be constructed otherwise. Various surface treatments or finishes may be desirable. In the case of a NiTi (Nitinol) or another metallic material implant, an electro-polished surface may be preferred.

Collapsed and expanded states of a heart valve can be controlled by varying the position and/or tension applied to the draw lines. A customized handle may be provided for the user interface. Draw line tension can be increased until the heart valve frame is fully collapsed and fully releasing the draw line tension allows the self-expanding heart valve frame to fully expand. The heart valve frame may be put in an intermediate state by varying the tension applied to the draw lines. Moreover, the system can be set up to allow a range of lateral control of the stent position during delivery. In one variation, a "joystick" control interface is provided; in another a model of the implant (or at least the stent frame portion of the valve to be delivered) is used.

In yet another delivery system embodiment allowing for delivery, repositioning, and/or percutaneous retrieval, different means or entities are provided to control the state of device deployment (variably, from fully collapsed to fully expanded) of the proximal end of a self-expanding heart valve device. Such means or entities pertain to the use of multiple sleeve or sheath features (herein optimally referred to as "zip tube" parts or an assembly with "zip tube" sheaths or fingers) provided to mechanically change an angle between adjacent strut elements and thereby the proximity of the struts. In use, the zip tube sheaths (or fingers) collapse the heart valve frame by "zipping" the struts into closer proximity.

In this embodiment, the ends of a self-expanding heart valve frame are configured with a link feature. A self-expanding retainer is constructed and configured with diametrically collapsible retainer arms or fingers. A zip tube part or assembly with diametrically expandable/collapsible sheath fingers is configured in such a manner to allow the zip tube fingers to slide over the retainer fingers. The ends of the retainer fingers are configured with a clasp or link feature so as to mate to the heart valve frame clasp or link features.

The zip tube assembly may be partially advanced (distally) to trap the heart valve frame and retainer such that they will not unlink because the inner diameter (or inner dimension(s)) of the zip tube fingers are constructed so as to constrain the linked heart valve frame and retainer from unlinking when positioned around the linked frame or retainer. With the retainer serving as a means to secure the valve in position, the zip tube assembly may be variably advanced (relative to the linked heart valve frame or retainer) to variably (e.g., partially) collapse the proximal end of the heart valve device or fully advanced to fully collapse the proximal end of the heart valve device.

The zip tube part assembly may be variably retracted to allow the proximal end of the self-expanding heart valve device to variably (partially) expand or retracted sufficient to allow the self-expanding heart valve device to fully expand. Alternatively, the zip part or assembly may be secured in position and the retainer may be variably retracted to variably collapse the proximal end of the heart valve device up to fully collapsed or variably advanced to allow the self-expanding heart valve device to variably expand up to fully expanded. The zip tube part or assembly can be fully retracted allowing the heart valve frame and retainer to unlink thereby releasing the heart valve device from the delivery system so that the heart valve device may be left in position and the delivery system may be removed.

In addition, any of the subject delivery system architectures may incorporate a visualization system for image-directed heart valve delivery (see FIG. 16B or 21A). Alternatively, other features for restraining and/or manipulating a self-expanding stent frame or a ballooned stent frame approach may be employed in an image-guided system. All of these embodiments involve a catheter or catheter-like device that utilizes an integrated imaging modality with a deployment mechanism (see FIG. 16B or 21A). As such, these embodiments may be used to accurately deploy a heart valve into a patient with greater accuracy and precision than with current procedural imaging modalities where direct visual confirmation is not possible.

In these embodiments, the delivery system (i.e., a delivery catheter comprising an implantable heart valve) incorporates a catheter-based imaging modality (e.g., an ultrasound imaging catheter) within the device (see FIG. 16B or 21A for a combined system depictions), such as, but not limited to, intravascular ultrasound (IVUS), intravascular photoacoustic (IVPA) imaging, optical coherence tomography (OCT), raman spectroscopy, or an optical method, capable of detecting features of a vessel in which the catheter is inserted. The selected imaging systems allow clinicians to image both the surrounding anatomy and the advancing catheter in real-time during the procedure (see FIG. 21B).

In one example, since IVUS is a tomographic imaging modality, a 3D image of the aortic root can be produced through pull-back imaging. High-resolution IVUS is well-known for interrogating the lumen wall of vessels and has also been used to visualize metal stents in vivo. In the example of IVUS hardware, a physician can accurately image and position the implantable valve device without the use of ionizing radiation or nephrotoxic contrast agents. Furthermore, IVUS advantageously provides for a real-time imaging modality.

A catheter system can be based upon an imaging catheter or a valve delivery catheter. In an embodiment where the catheter system is based upon the valve delivery catheter, the imaging modality device can be inserted through the center of the valve delivery catheter (FIGS. 16B and 21A), where the active imaging element is aligned with a feature of the valve delivery catheter, such as, but not limited to the catheter tip, the distal or proximal end of the valve stent, or some other predetermined landmark of the valve delivery catheter. Positioning of the imaging device on the circumference of the valve delivery catheter is also possible in another embodiment to prevent visual hindrance from the implanted stent.

In yet another embodiment, the valve delivery system is based upon the imaging catheter, and the deployment mechanism is inserted through the lumen of the imaging catheter, such as, but not limited to, through a guidewire port of the imaging catheter. Furthermore, the delivery system referred herein is not limited to the delivery of a heart valve device, but could be used to deliver therapy to a localized region through the use of a catheter. Such examples of delivery could include, but are not limited to, delivery of drugs or other therapeutic agents, delivery of RF irradiation, or delivery of another device.

Operation of the delivery system allows visualization of the surrounding anatomy during insertion of the imaging catheter in the context of the location of the delivery catheter. As such, the location of the delivery catheter relative to the surrounding environment may always be known. In one embodiment, the delivery system is fixed relative to the imaging transducer within the catheter. In another embodiment, the two components can be moved relative to one another (FIG. 21B). However, in embodiments where relative motion is allowed, the relative motion is advantageously tracked or known in order to maintain accuracy in the advancing catheter.

The subject delivery devices, kits in which they are included (with and without valve installation or assembly), methods of use and manufacture (such as assembly of the delivery system and frame alone and/or with included valve) are all included within the scope of the present disclosure. Some aspects of the same are described above; more detailed discussion is presented in connection with the figures below.

Other systems, devices, methods, features, and/or advantages of the subject matter described herein will be or will become apparent to one with skill in the art upon examination of the following figures and detailed description. It is intended that all such additional systems, devices, methods, features, and/or advantages be included within this description and be within the scope of the subject matter described herein, regardless of whether recited in this summary section. In no way should the features of the example embodiments in this or any other section be construed as limiting the appended claims, absent express recitation of those features in the claims.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely. Variations other than those shown in the figures are contemplated as described in a broader sense in the above summary section, as generically claimed, or otherwise.

Figures 5A, 5B, 5C, 5D, 5E:
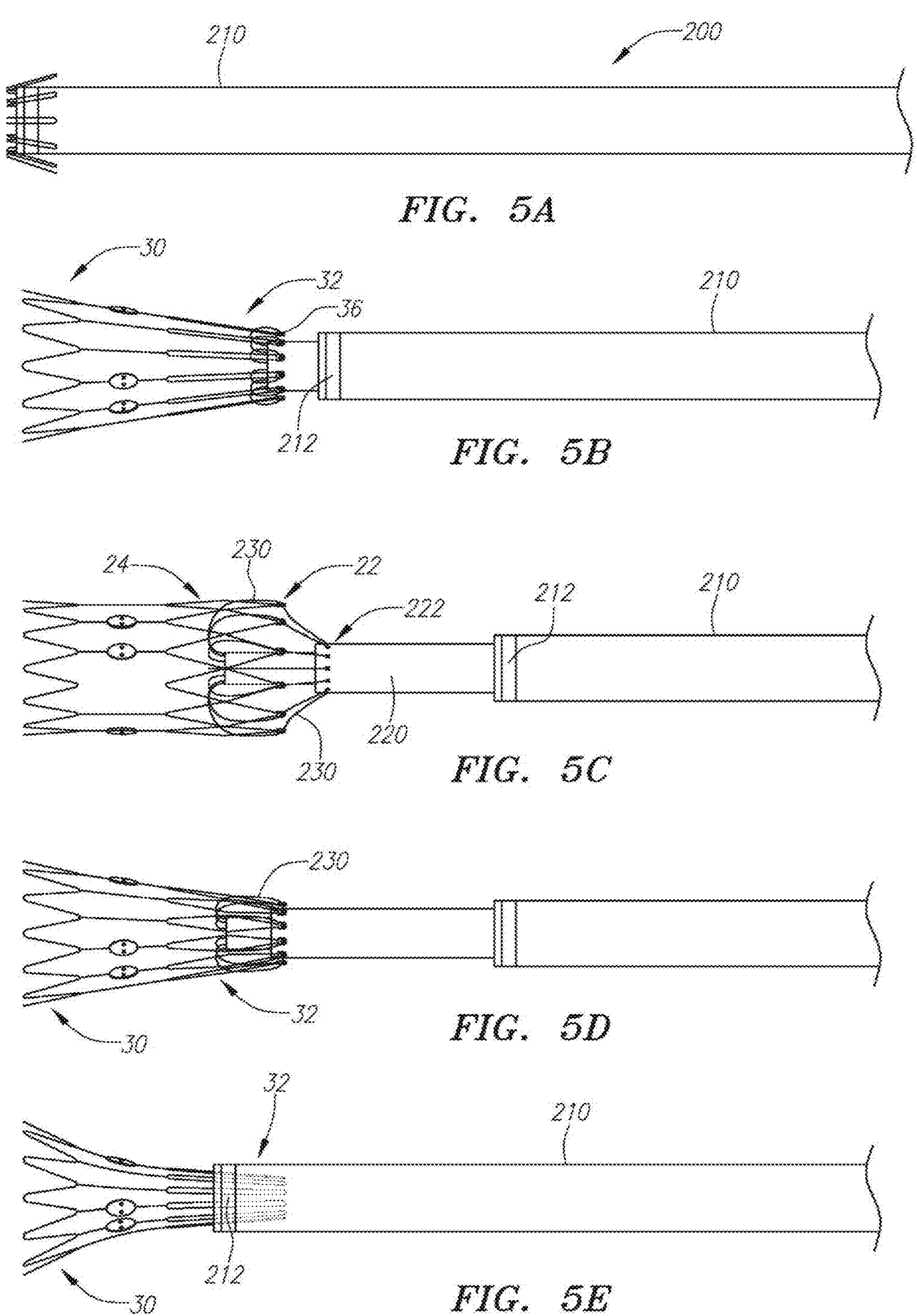
Figures 6A, 6B, 6C:
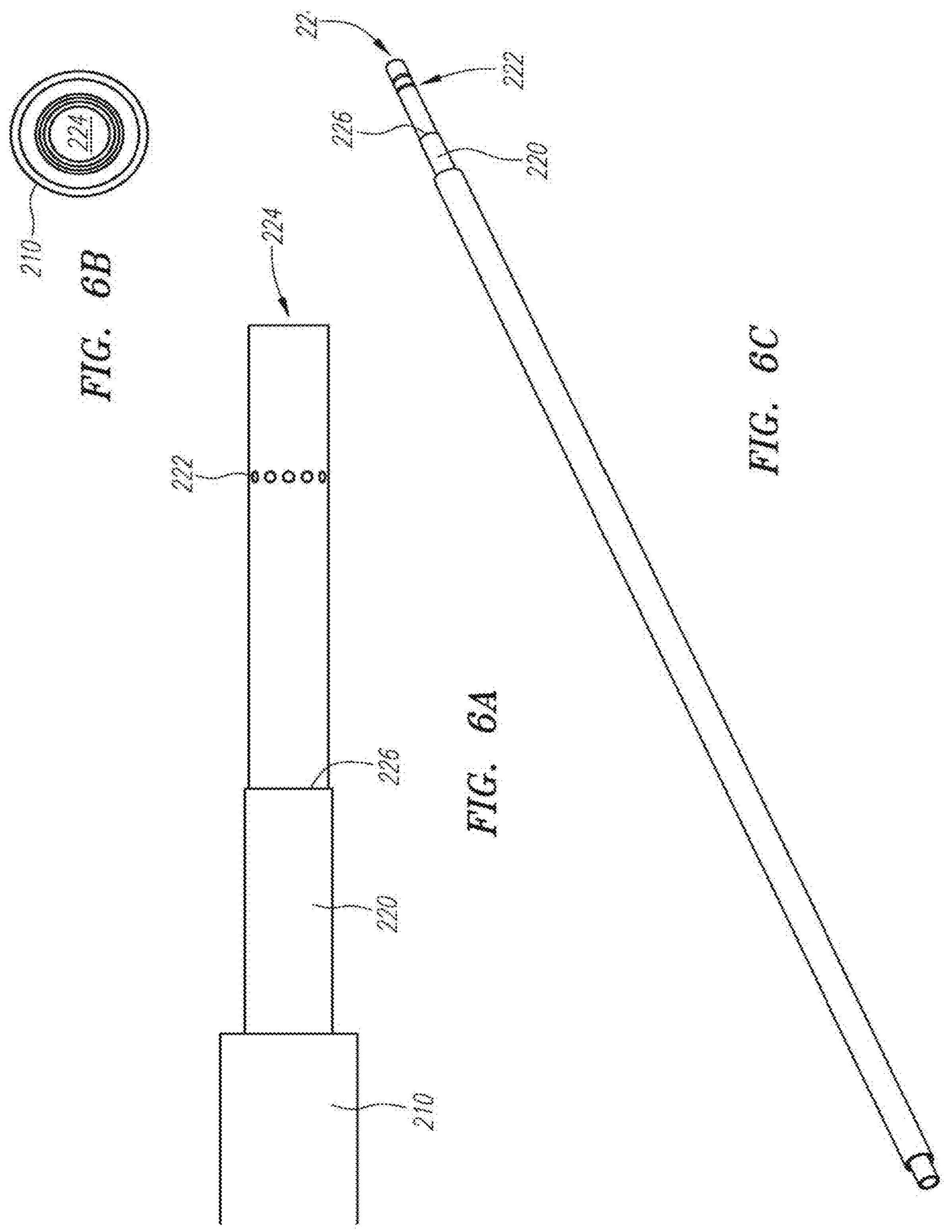

FIGS. 5A, 5B, 5C, 5D, and 5E illustrate progressive stages of stent frame deployment and recapture for a second embodiment FIGS. 6A, 6B, and 6C illustrate side, end, and perspective views, respectively, of the delivery device sleeve of the second embodiment.

Figure 7A:
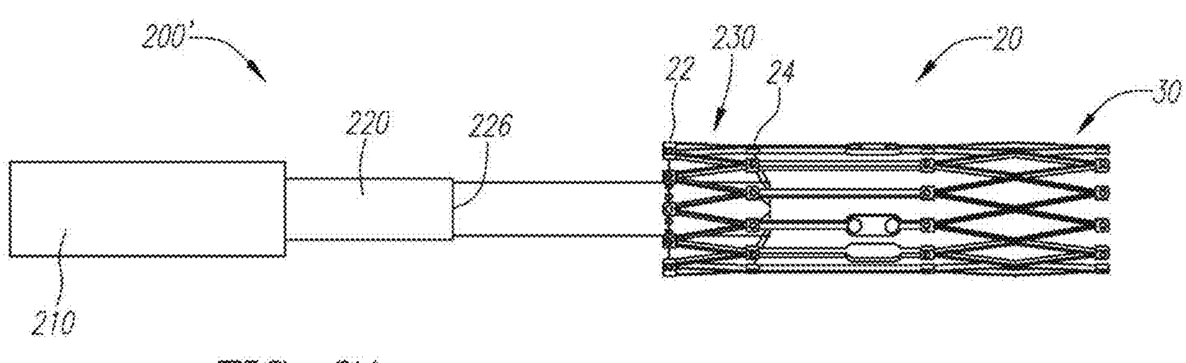
Figure 7B:
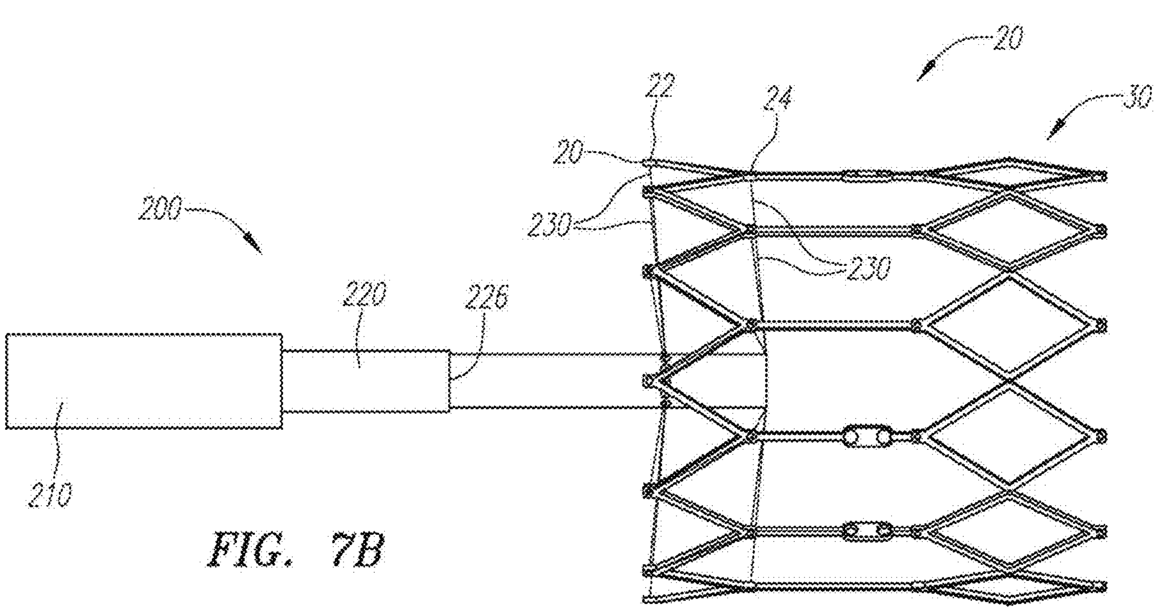

FIGS. 7A and 7B are side views illustrating the sent frame associated with the delivery device sleeve in contracted and expanded states, respectively.

Figures 8A, 8B, 9A:
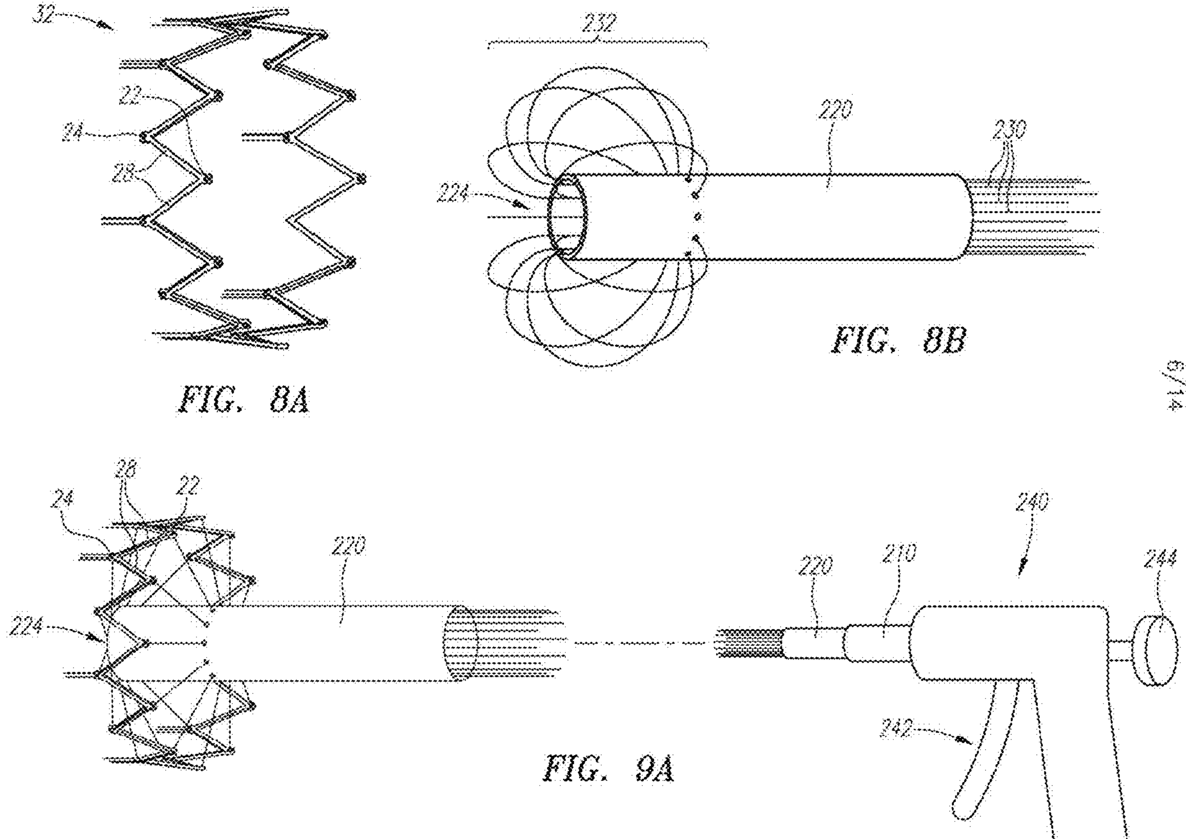

FIG. 8A illustrates a variation of the subject stent frame and FIG. 8B illustrates a variation of the subject delivery sleeve with associated draw line filaments FIGS. 9A, 9B, and 9C are side, perspective, and end views, respectively, illustrating the components in FIGS. 8A and 8B assembled together.

FIGS. 10A and 10B are side and end views, respectively, illustrating the same assembled components shown in a compressed state.

Figures 11A, 11B, 12, 13A, 13B:
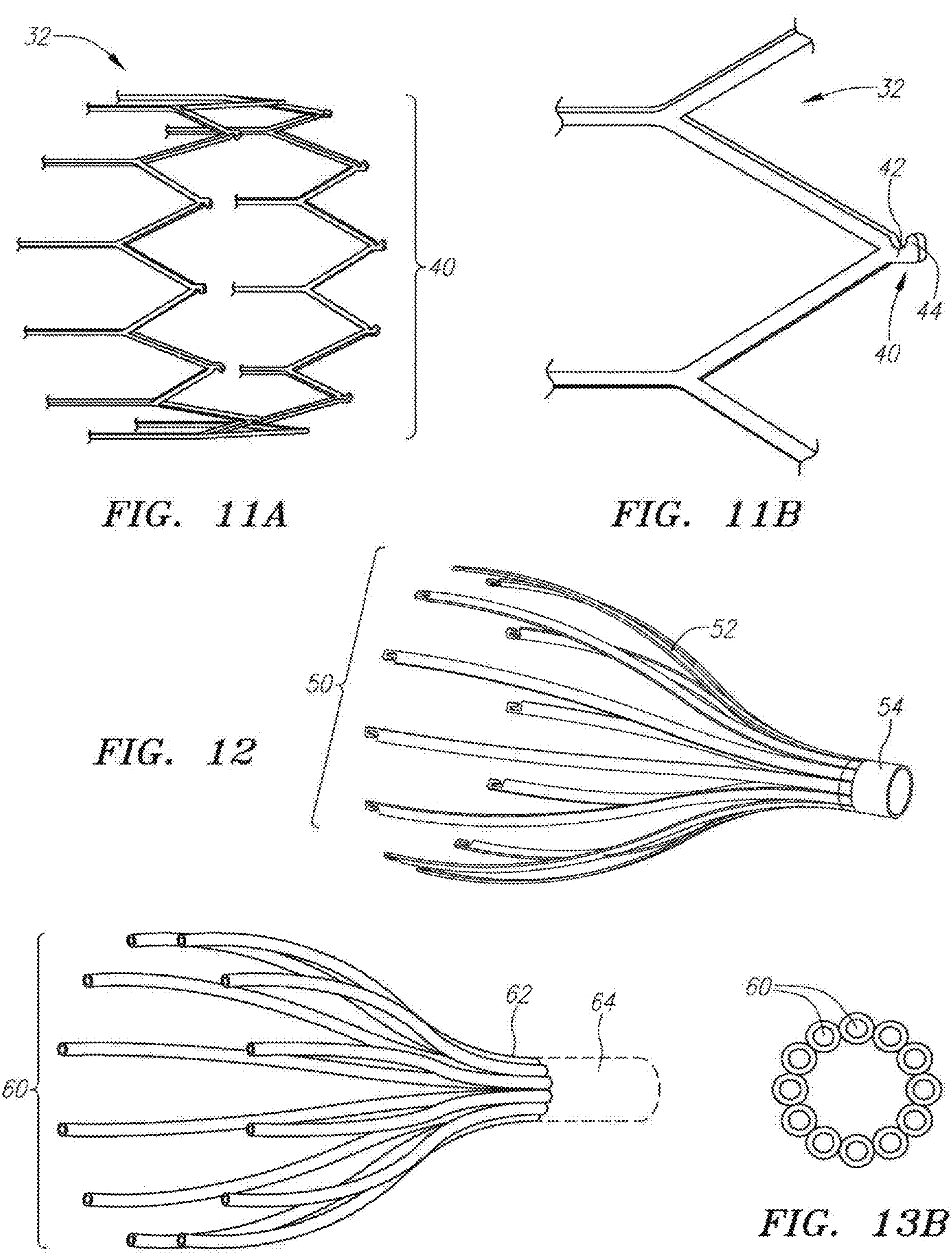

FIGS. 11A and 11B are partial perspective and detail side views, respectively, illustrating a stent frame for a third embodiment.

FIG. 12 is a perspective view illustrating a frame retainer with retainer fingers.

FIGS. 13A and 13B are perspective and end views, respectively, illustrating a zip tube part or assembly and zip tube fingers.

Figure 14A:
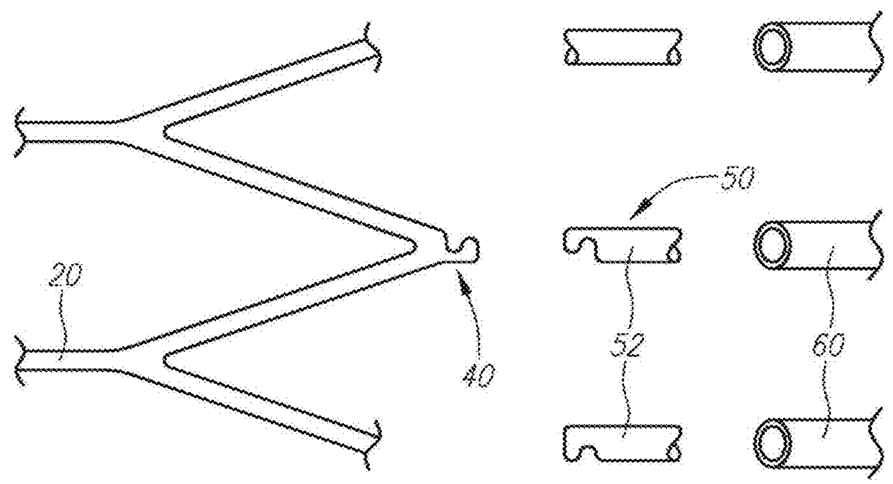
Figure 14B:
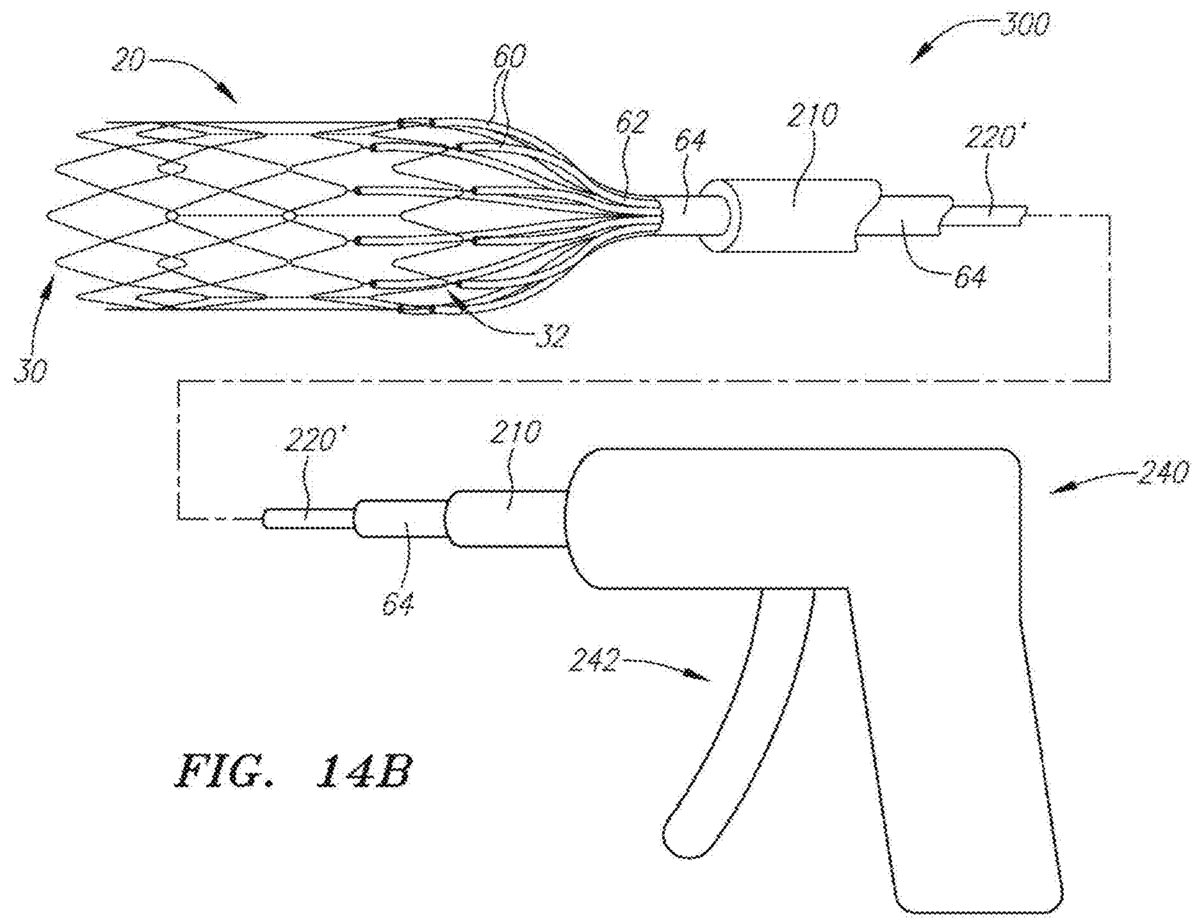

FIG. 14A illustrates segments of an expanded heart valve frame, retainer fingers, and zip tube fingers as associated in the subject embodiment and FIG. 14B illustrates a complete assembly of the embodiment including these subcomponents.

FIG. 15A, 15B, 15C, 15D, 15E, 15F are detail side views illustrating operation of elements within the embodiment.

Figures 16A, 16B, 17:
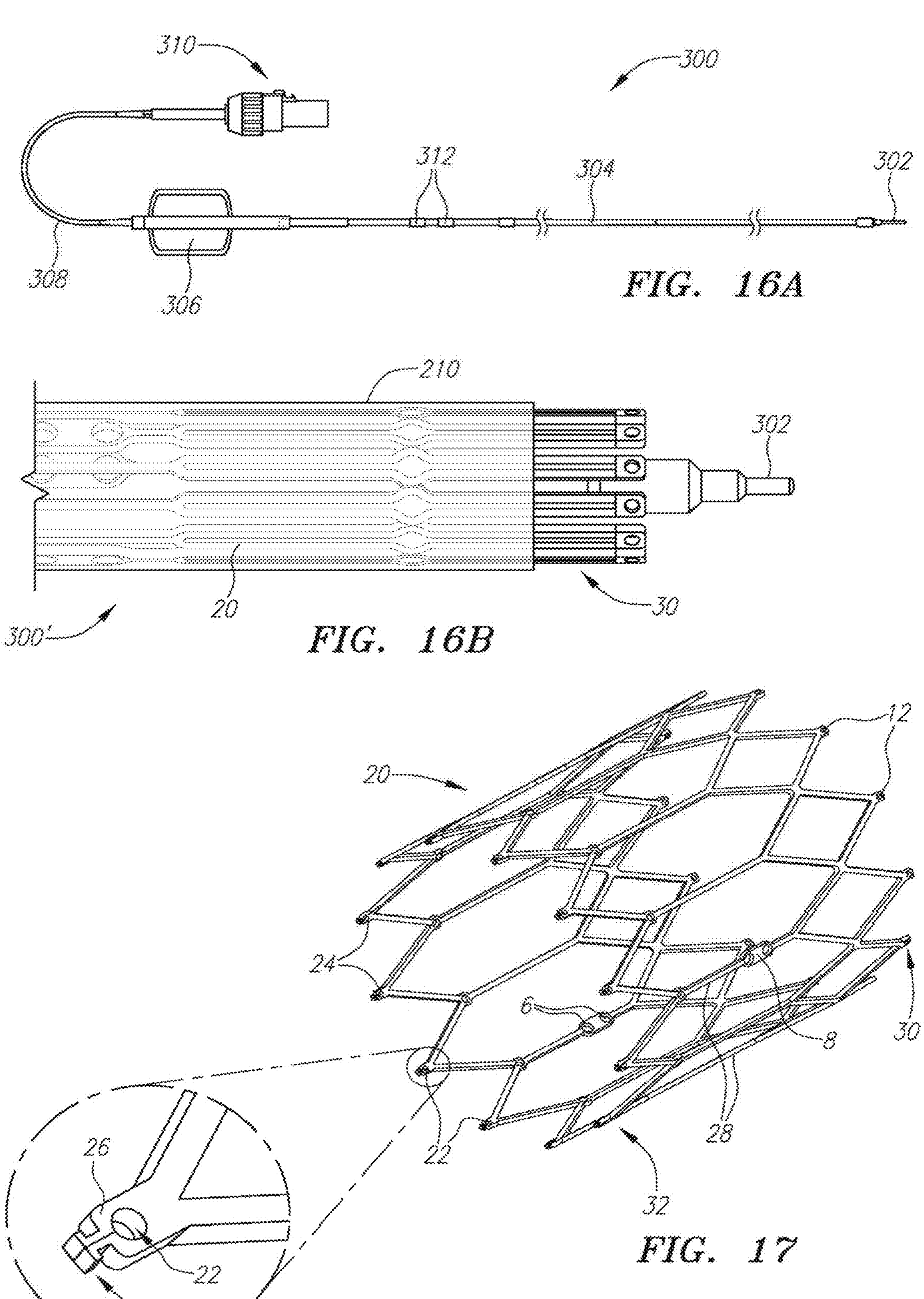

FIGS. 16A and 16B are side views illustrating an example embodiment of imaging catheter and stent frame components of an image-guided delivery system.

FIG. 17 is an enlarged perspective view of a stent frame component as previously illustrated.

Figures 18A, 18B:
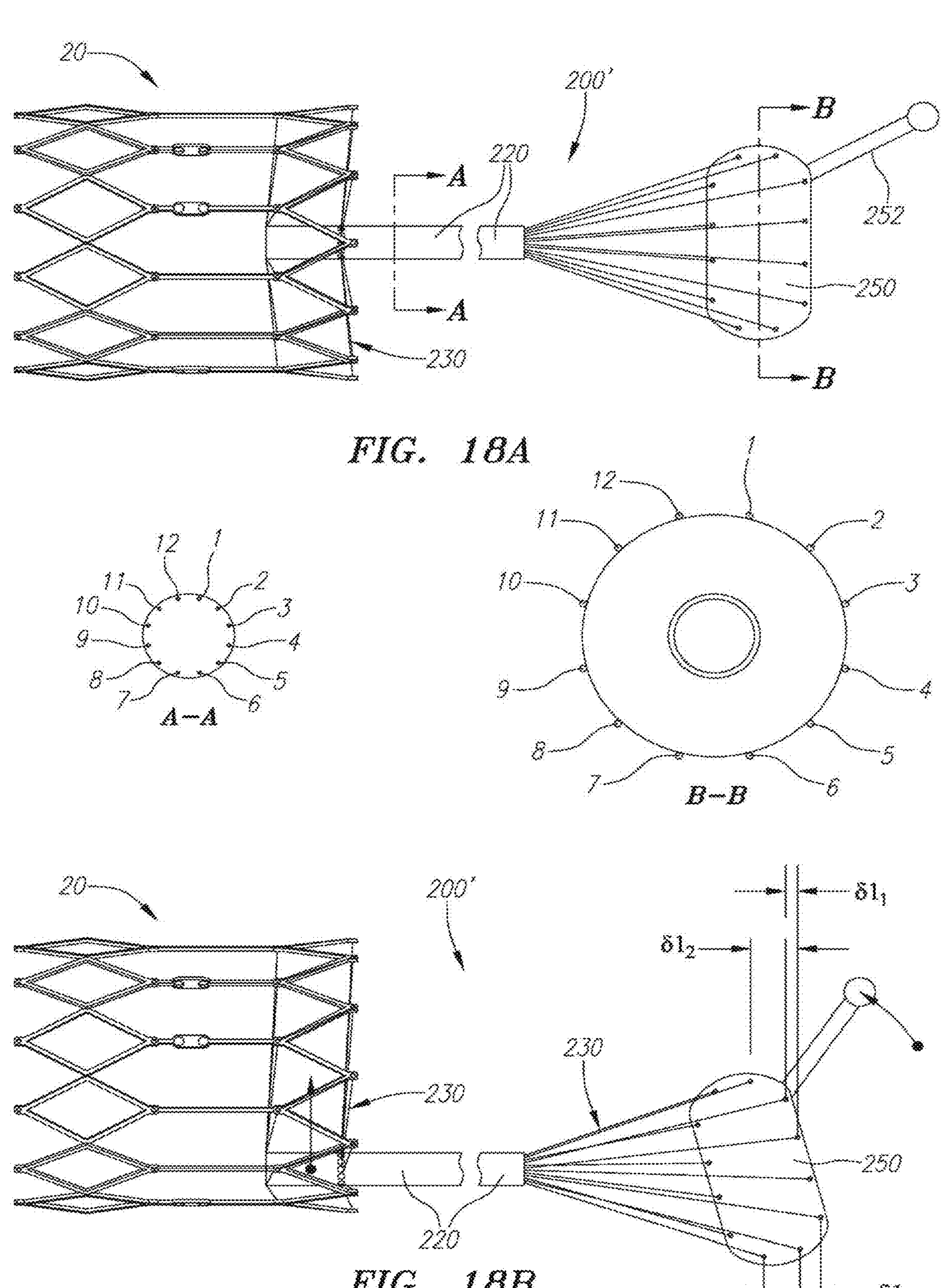

FIGS. 18A and 18B are side views illustrating the stent frame embodiment of FIG. 17 associated with a delivery device, with the stent frame in a neutral and a laterally displaced position, respectively.

Figures 19A, 19B, 20:
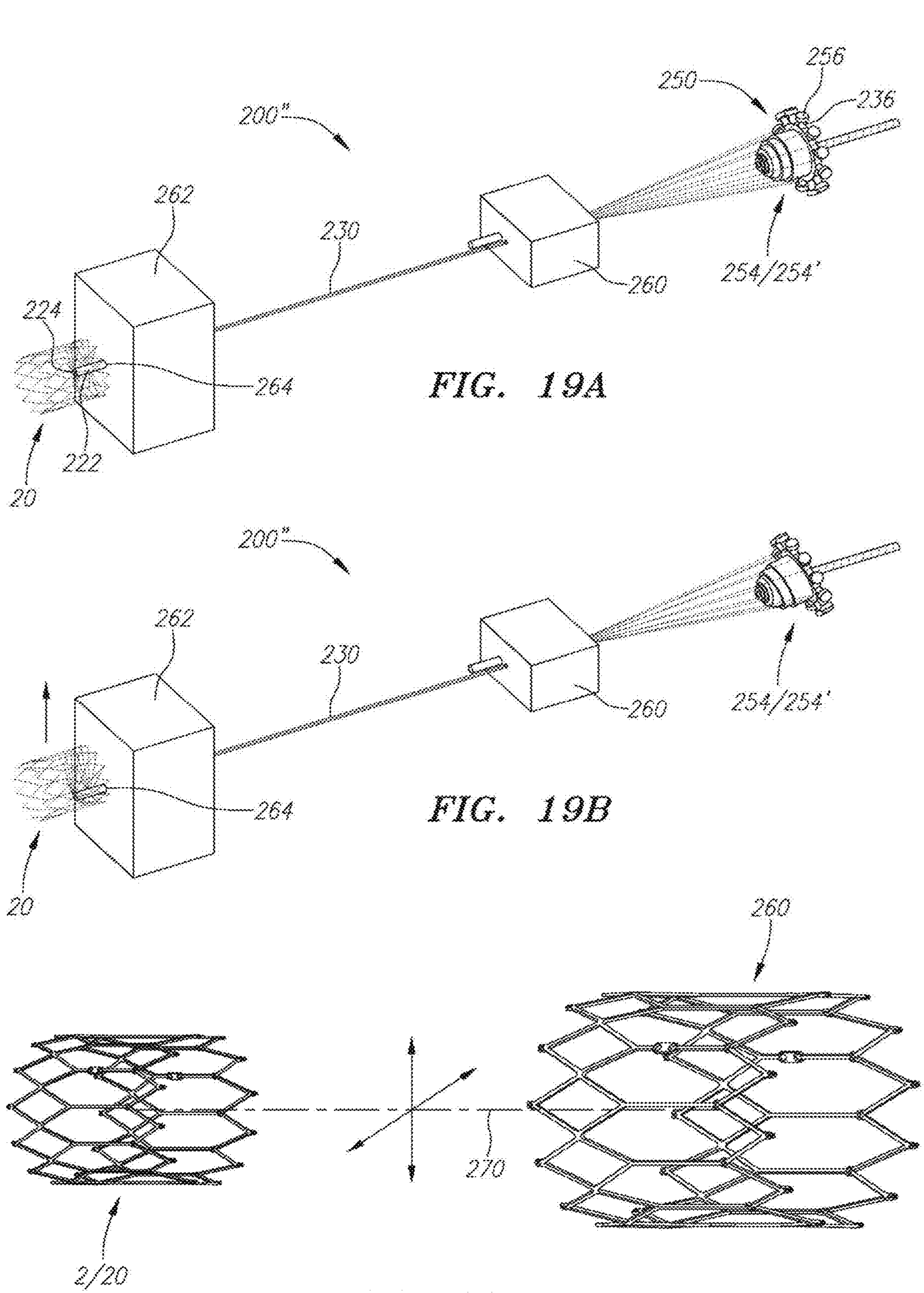

FIGS. 19A and 19B are photographs illustrating prototype hardware of the delivery system embodiment diagrammatically illustrated in FIGS. 18A and 18B.

FIG. 20 diagrammatically illustrates an alternative user interface for the FIGS. 18A and 18B delivery system.

Figure 21A:
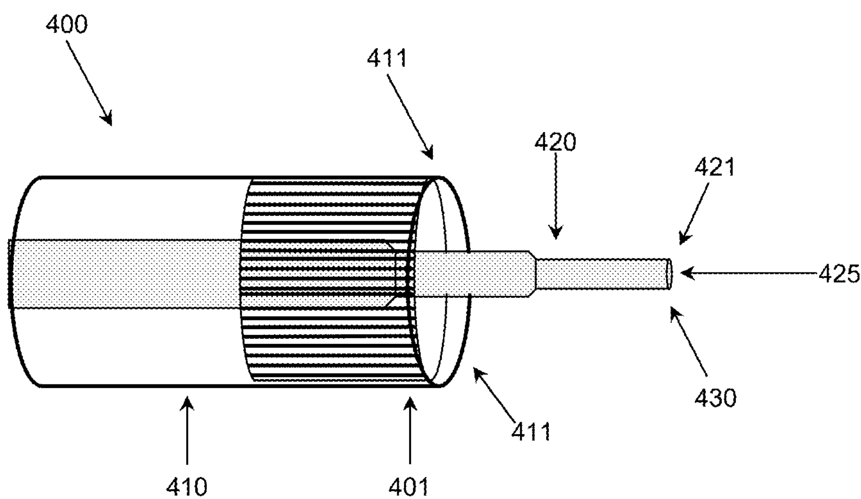
Figure 21B:
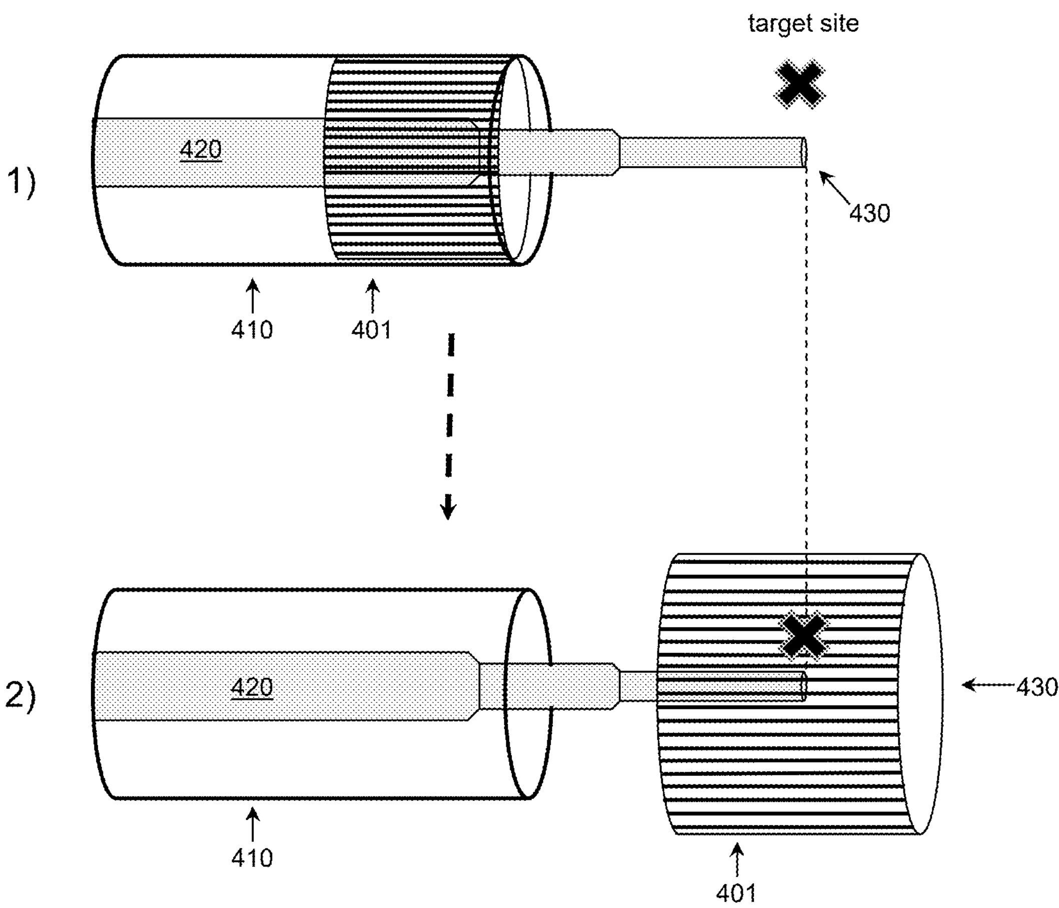

FIGS. 21A and 21B shows an overview of the devices as described herein. FIG. 21A illustrates an example embodiment of a combined system as shown in FIG. 16B comprising an imaging catheter within a delivery catheter comprising an implantable heart valve of an image-guided delivery system as described here. FIG. 21B demonstrates the mechanism in which an implantable heart valve is positioned at a target site: 1) the ultrasound imaging transducer located at a distal end of the ultrasound imaging catheter is moved towards and positioned at the target site (i.e., the site in which the heart valve is to be placed); 2) the ultrasound imaging transducer remains stationary while the implantable heart valve is pushed forward towards and exits through the distal end of the delivery catheter for deployment at the target site; this ultimately allows for the expanded, deployed valve and transducer to be at target site simultaneously.

DETAILED DESCRIPTION OF THE INVENTION

Various example embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the various embodiments. In addition, many modifications may be made to adapt a particular situation, material, composition of matter, process, process act, or step to the objective(s), spirit, or scope of the present inventive subject matter. All such modifications are intended to be within the scope of the claims made herein.

The present invention features a delivery system (400) comprising an implantable heart valve (401), a valve delivery catheter (410) comprising a first lumen (415), and an ultrasound imaging catheter (420) inserted through the center of the first lumen (415) of the valve delivery catheter (410) (see FIG. 16B or 21A). The valve delivery catheter (410) may be reversibly coupled with the implantable heart valve (401) at a distal end (411) of the valve delivery catheter (410). In some embodiments, the ultrasound imaging catheter (420) comprises a guide wire lumen (425) and an ultrasound imaging transducer (430) located at a distal end (421) of the ultrasound imaging catheter (420). The ultrasound imaging catheter (420) may be configured to moveably pass: (i) over a guide wire passing through the guide wire lumen (425) of the ultrasound imaging catheter (420), (ii) through the first lumen (415) of the valve delivery catheter (410), and (iii) through the implantable heart valve (401) (see FIG. 16B or 21A).

In some embodiments, the ultrasound imaging transducer (430) can be movably positioned to capture images of a surrounding anatomy, the valve delivery catheter (410) and the implantable heart valve (401) in real time during delivery of the implantable heart valve (401) in a subject. In some embodiments, the ultrasound imaging transducer (430) remains stationary while the implantable heart valve (4010 is pushed forward towards and exits through the distal end (411) of the delivery catheter (410) for deployment as seen in FIG. 21B.

In some embodiments, the implantable heart valve (401) comprises a self-expandable stent frame. The implantable heart valve (401) may comprise a prosthetic aortic valve and the delivery catheter (410) is adapted for transcatheter aortic valve replacement (TAVR) applications. In some embodiments, the position of the implantable heart valve (401) can be viewed circumferentially and in an axial direction. In some embodiments, the ultrasound imaging catheter (420) comprises radiopaque shaft markers that are coordinated with corresponding markers on the valve delivery catheter (410).

FIGS. 1A-1F illustrates an implant 2 and a suitable approach to valve 10 attachment and its manipulation for delivery in coordinated use with an expandable stent frame 20. Further details as to valve construction and/or its manipulation for delivery may be appreciated in review of U.S. Pat. No. 8,133,270 to Kheradvar, et al., incorporated by reference herein in its entirety for all purposes. Features of the stent frame elaborated upon below in the various embodiments may be added to those shown in FIGS. 1A-1F or used in connection with other suitable stent frames and/or other valve architectures.

Figures 1A, 1B, 1C, 1D, 1E, 1F:
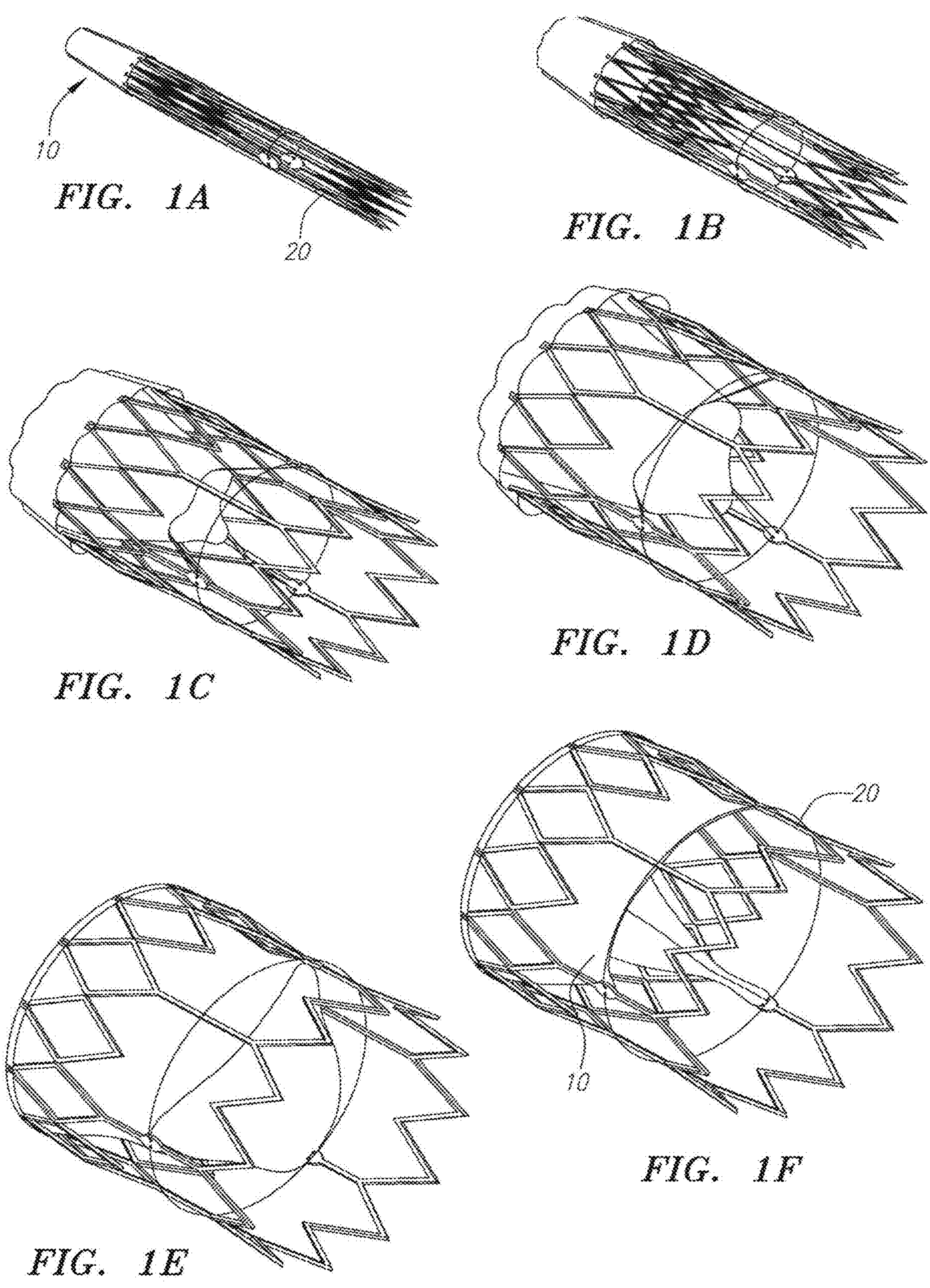
FIGS. 1A, 1B, 1C, 1D, 1E and 1F are perspective views illustrating an example embodiment of a stent frame and valve in various stages of deployment as may be employed in connection with the embodiments herein.
Figures 2A, 2B, 3, 4A, 4B:
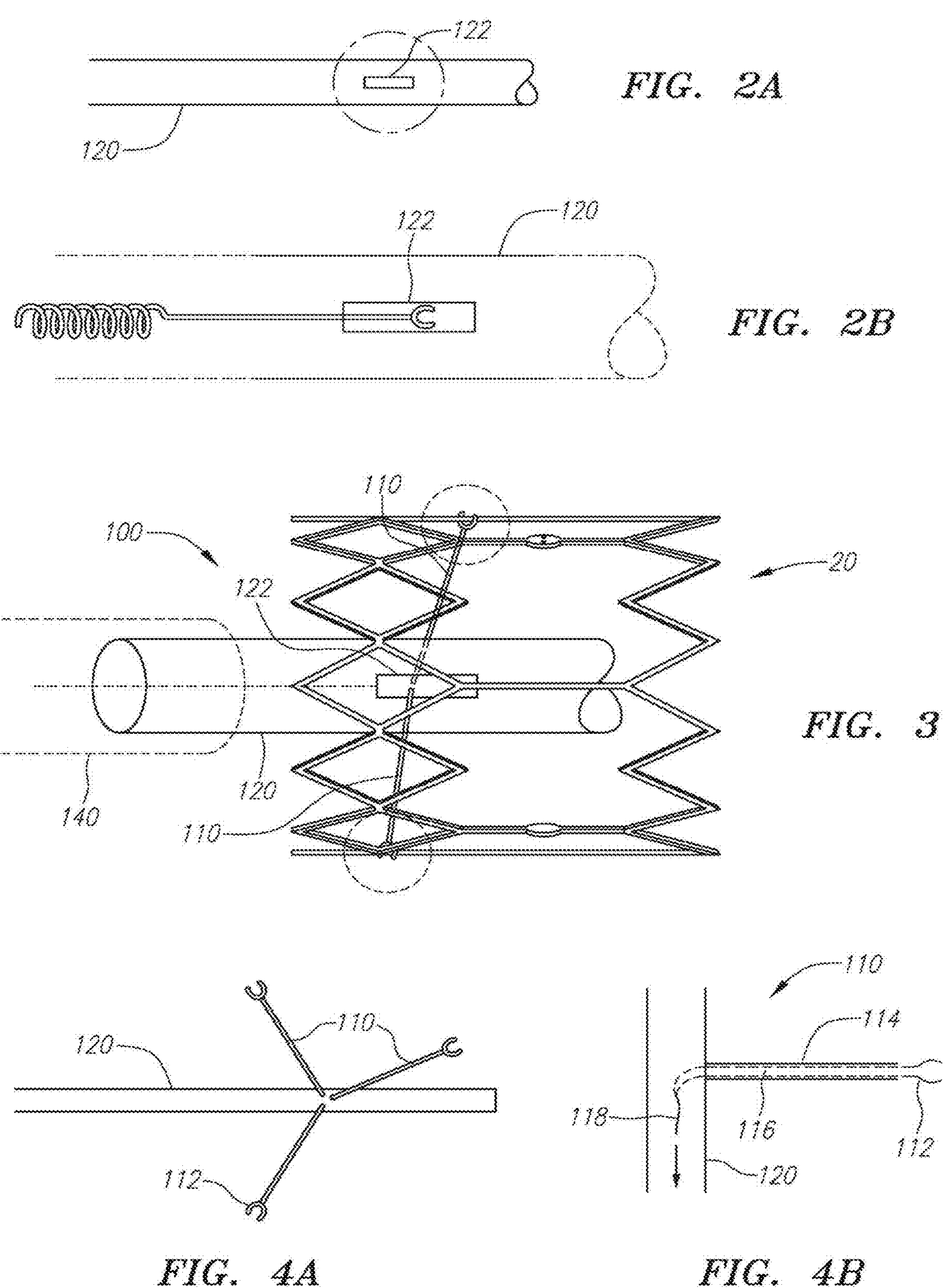
FIG. 2A is a detailed view illustrating the delivery device sleeve of a first embodiment showing the location of one of a plurality of embedded arms.
FIG. 2B is a detailed view illustrating the arm at the location in FIG. 2A connected to a spring system for controlling stent frame deployment
FIG. 3 is a system overview illustrating the arms releasably attached to a stent frame.
FIG. 4A is a detailed view illustrating the arms fully extended from the delivery apparatus and FIG. 4B is a detailed view illustrating a hollow deployment arm with strings inside and a pull/push mechanism inside the guide tube or sleeve.

In any case, implant 2 (e.g., valve 10 and stent frame 20) is directly applicable for coordinated use with a delivery system as shown in FIGS. 2A-4B. More specifically, a delivery system apparatus for controlled deployment of a stented heart valve system in increments is shown. The system provides for repositioning a stented heart valve system during and after deployment. As variously illustrated, device 100 includes a plurality of deployable arms 110. These are adjustably deployable. The arms are first embedded inside the apparatus. FIG. 2B illustrates the location of one of the embedded arms 110 within a delivery device sleeve 120. For tracking to the target site, the arms are hidden. The arms exit the sleeve through ports or slots 122 in the wall of the sleeve. The arm lengths are adjustable and the arms are releasably attached to the stent of the stented valve. As shown in FIG. 2B, each arm may be equipped with an in-line adjustable spring that is controllable by the operator remotely. As illustrated in FIG. 3, such actuation allows for robust radial expansion or deployment of the collapsed stent frame in increments.

The arms remain attached to the stent until the stent is fully deployed. During tracking to a site for deployment, the stented valve may be covered by a sheath incorporated in the delivery system or pass within a delivery catheter (either case illustrated by an optional sleeve 140). If the stent is not properly deployed, the arms, which are still releasably attached to the stent, can be used for partial contraction of the stent for repositioning purposes. When the stented valve is properly positioned within the heart, the arms will be released from the stent, and return to their embedded positions within the apparatus. Then the apparatus will be retracted into the sheath or through the delivery catheter from the heart or vasculature.

As seen in FIG. 4A in which the stent frame is detached, each arm may terminate in a releasable hook, jaw, clevis 112 or the like for such purpose(s). The connection and release may be provided by a simple snap fit. Otherwise it may be provided by a more active means for stent frame interface as illustrated in FIG. 4B, that shows an arm comprising a hollow micro tube or sheath 114 with spring loaded strings or filaments 116 inside where a string or filament 118 inside the guide tube or sleeve 120 can be used to control the closing and opening of the hooks 112.

FIGS. 5A-5E illustrates progressive stages of implant deployment and recapture for a second embodiment. Here, in a system pictured for over-the-wire tracking to its deployment site, a delivery system 200 includes a sheath 210 (with distal radiopaque marker 212) coaxial with a pusher sleeve 220. A distal portion of sleeve 220 includes apertures 222 through which filaments 230 pass into and proximally within the length of the sleeve. The filaments loop from these apertures through proximal stent frame apertures 22 and more distal stent frame apertures 24 (or alternatively past strut junctions in a different stent configuration) and into a distal end 224 of the sleeve (or a second set of distal apertures (not shown) in the sleeve if so-desired). Such details of the sleeve are shown unobscured in FIGS. 6A-6C, as is an optional shoulder 226 for abutting proximal end or crown sections 26 of the stent frame and guide sheath 210 of the proximal end or crowns of the stent frame.

Regarding interaction between the stent frame and delivery system 200, FIGS. 7A and 7B provide side views of the stent frame associated with the delivery device sleeve in contracted and expanded states, respectively. Here, the manner of stent frame expansion and contraction as related to extended filament 230 length is clearly visible FIGS. 8A and 8B further illustrate such details as described above. When assembled in a delivery system 200, stent frame 20 will be captured within loops 232. The assembled relation of elements is shown in each of FIGS. 9A-9C and FIGS. 10A and 10B. Comparing FIGS. 9A-9C to FIGS. 10A and 10B, the state of the stent frame is changed from open or expanded in the former trio of figures, to compressed in the latter pair.

Such control is achievable by remote actuation of the loop filaments with a customized handle or other user interface means. Any handle may include means for group control of the filaments and independent control of sheath position. Such a handle 240 may include separate "grip" 242 and "plunger" or "slide" 244 interfaces as illustrated by example in FIG. 9A for such purposes. Otherwise, mechanisms internal to the handle can automate all of the various control procedure(s) by actuating a grip 242, alone.

FIGS. 9A and 9B also offer good illustration of the manner in which filaments 230 pass through apertures 22, 24 and run along interposed strut sections 28. FIG. 9C illustrates the radial relationship of the apertures and filament 230 portions. Here, a crossing segment 234 of the filament between the apertures 22 and 24 is positioned outside of an opposing strut section 28. The crossing segments are angled with the struts when the stent frame is in an expanded state and more close to axially aligned when the stent is compressed as shown in FIGS. 10A and 10B.

As noted above, the transition between the open and compressed states (and states therebetween) is managed by letting-out or reeling-in the draw line filament determining the size of the control loop. Ultimately, one end of the line is pulled all of the way through the stent aperture to finally release the implant.

FIGS. 5A-5E illustrates a range of activity that is possible in terms of device manipulation before such release. In succession, these views show progressive stent frame deployment and steps toward complete recapture. FIG. 5A pictures (literally, given that the figures are based on photographs) the beginning of stent frame deployment as sheath 210 is withdrawn and a distal end 30 of the stent self-expands. FIG. 5B shows the sheath fully withdrawn and full tension on the draw lines or filaments, maintaining a proximal side 32 of the stent 20 in a compressed state. As in FIG. 5D illustrates the same (but in the case of FIG. 5D re-compression after the relaxation of draw lines to allow expansion as in FIG. 5C), the sheath can be advanced to fully recapture the stent frame. With the beginning of such action shown in FIG. 5E, the stent frame can be fully recovered within sheath 210—whether for the purpose of repositioning or bulk retrieval of the device.

A third delivery device embodiment is able to offer similar advantages in terms of delivery, repositioning, and/or percutaneous retrieval. Stent frame components of such a system are shown in FIGS. 11A and 11B. In each view, a proximal end 32 of a stent frame 20 includes clasp features 40. Each clasp feature 40 may comprise a bridge section 42 and an overhang section 44. Complementary clasp features 50 are provided at the end of resilient retainer "arms" or "fingers" 52 associated with a delivery system pusher. Arms 52 may comprise Nitinol or another elastic or superelastic material. Arms 52 are biased outward such that they spring out to a position as shown in FIG. 12 when released from restraint (e.g., upon exiting a delivery system sheath element or delivery/guide catheter body). Arms 52 are joined or meet at a hub 54. These components may be cut from a single hypotube or polymer sleeve that extends to the proximal end of the delivery system (not shown) as one piece or be assembled using conventional techniques such as laser welding, etc. In any case, pairs of complementary clasp elements 40/50 are releasably engaged in sheaths 60.

FIGS. 13A and 13B illustrate a construct in which multiple sheaths 60 extend to and join at a hub 62 optionally extending proximally as a single sleeve 64. Such a structure can be produced by bundling and reconfiguring (e.g., by fusing) a plurality of thermoplastic sheaths, bundling and bonding a plurality of sheaths, and splitting an end of a multi-lumen extrusion into a plurality of separate sheaths. Other means of construction will be appreciated by those of skill in the art as well.

Regardless, FIG. 14A provides a partial assembly drawing illustrating the axial alignment for a plurality of interfacing members. FIG. 14B shows the same components of the third device embodiment brought together in a completed apparatus assembly 300. As in the embodiments above, such a system may optionally include a cover sheath 210 and a handle 240. In addition, system 300 may include an innermost elongate sleeve 220' optionally providing a lubricious P1FE liner for a guidewire lumen and/or column or "push" strength to the system.

Figure 15A:
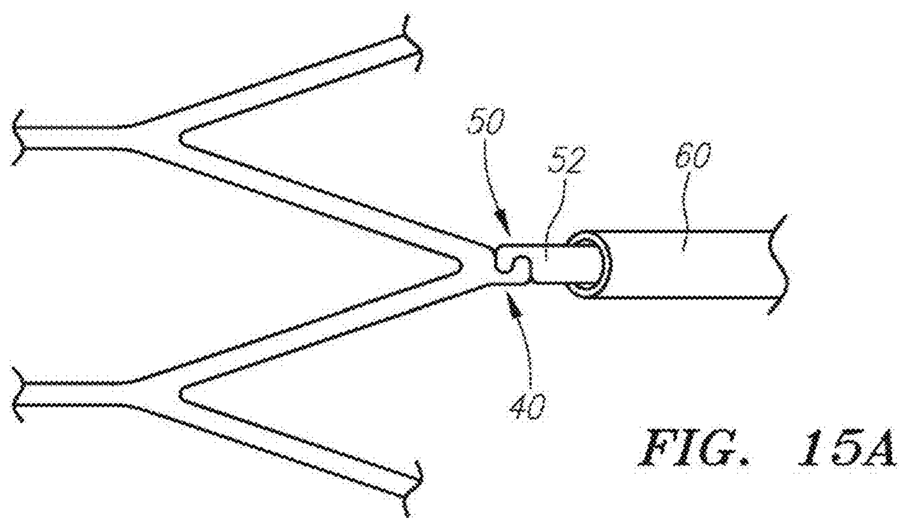
Figure 15B:
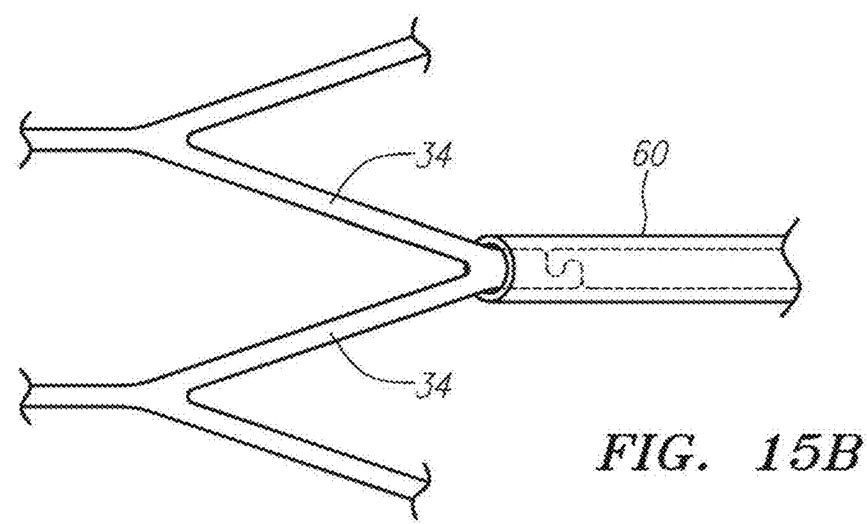
Figure 15C:
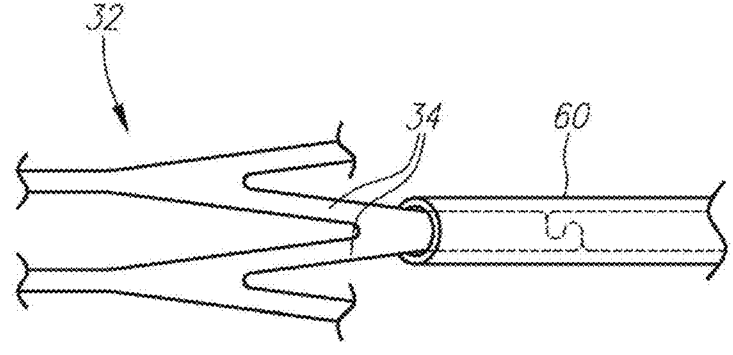
Figure 15D:
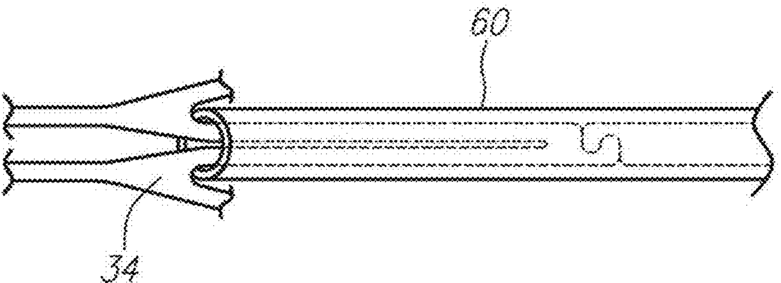
Figure 15E:
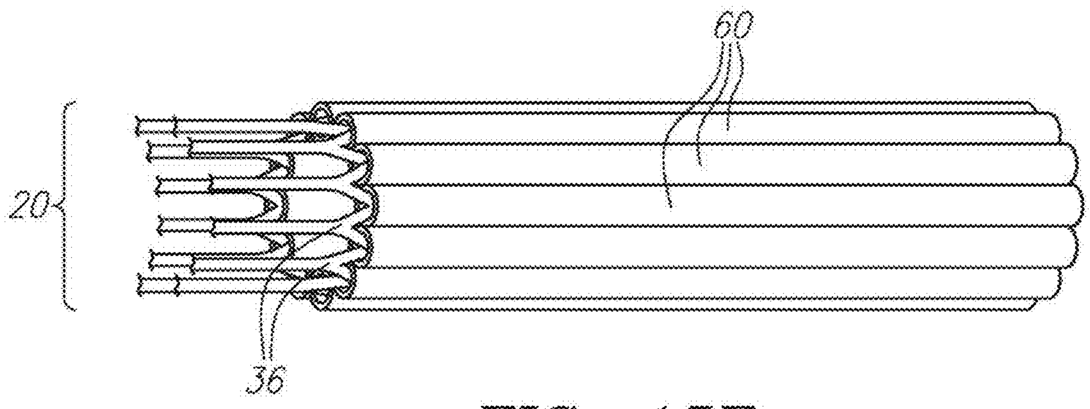

FIGS. 15A-15F illustrates the operation of an intended interaction of the subcomponents of system 300. In FIG. 15A, the heart valve frame clasp or link 40 is interfaced with clasp/line 50. In FIG. 15B, clasps features 40/50 are trapped within sheath 60. At this point, further withdrawal of stent frame 20 into sheath element 60 or (stated otherwise) advancement of sheath 60 over adjacent proximal stent struts 34 results in a condition as shown in FIG. 15C. Here, struts 34 are brought together collapsing the entirety of the proximal end 32 of stent frame 20 (given that the same condition is achieved around the entire periphery of the stent by paired device features). As shown in FIG. 15D, sheath 60 can cover the entirety of struts 34 up to their junctions 36 with adjacent struts. The net effect is shown in FIG. 15E where the entire proximal side of the stent frame 20 is compressed efficiently by the multiple sheath elements shown.

As summarized above, the zip tub part assembly (sheaths 60 and associated components) may be variably retracted to allow the proximal end 32 of the stent frame to partially expand or retracted sufficiently to allow the stent frame to fully expand. Alternatively, the zip part/assembly may be secured in position and the arm retainer 54 retracted to variably collapse the proximal end of the heart valve device (up to fully collapsed) or variably advanced to allow the self-expanding heart valve device to variably expand (up to fully expanded). Further action associated with collapse/compression and expansion of the stent frame is achieved by covering and uncovering the stent frame with optional sheath 210 or by a guide catheter.

Figure 15F:
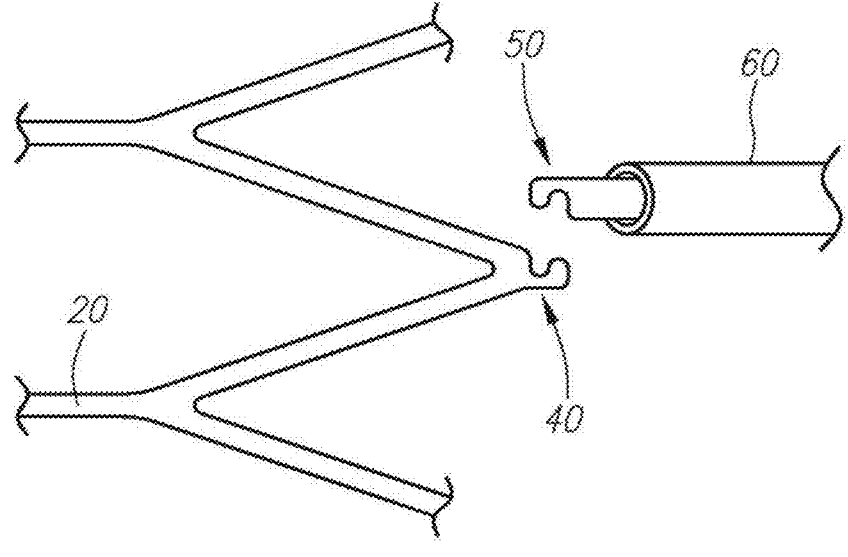

In any case, upon achieving desired implant placement, clasp elements 40/50 can be freed from confinement within the sheath member(s) 60 thereby unlinking the elements allowing stent frame 20 release as shown in FIG. 15F and allowing delivery system withdrawal from a patient in a successful percutaneous heart valve implantation procedure.

FIG. 16A illustrates a suitable IVUS catheter 300 for use in an image-guided valve delivery system according to another embodiment. The figure shows an EAGLE-EYE IVUS imaging catheter (Volcano Corp). Imaging catheter 300 includes a distal transducer tip 302, an intermediate catheter shaft or body 304, handle/grip 306, lead 308, and a proximal connector 310. Radiopaque shaft markers 312 are provided that may be relocated or additional markers added for coordination with a valve delivery catheter to (together) provide an overall valve delivery catheter system (e.g., by inserting catheter 300 within delivery system 100 or 200 as previously illustrated; see FIG. 16B or 21A for depictions of combined systems).

A distal portion of such a combined system 300' is shown in FIG. 16B. This photograph shows a distal end 30 of a TAVR stent 20 compressed to 4.3 mm diameter (13 Fr). It is held in a sheath 210 that may form part of an overall delivery system 300'. Otherwise, it may be regarded as a loading sheath or surrogate (or stand-in) for a delivery catheter through which the stent 20 will track in a medical procedure. As shown, an ATLANTIS SR PRO IVUS transducer (Boston Scientific Corp.) 302 is placed through the center of the valve stent frame 20 for sizing purposes. This combined systems as presented in FIG. 16B is further clarified in FIG. 21A. FIG. 21A shows a combined system (400), specifically highlighting the distal end of the system. As shown in FIG. 21A, an ultrasound imaging catheter (420) comprising a transducer (430) is inserted through a delivery catheter (410) comprising an implantable heart valve (401). This placement of the ultrasound imaging catheter (420) (i.e., through the first lumen (415) of the delivery catheter (410)) allows the ultrasound imaging catheter (420) to move freely through the delivery catheter and the implantable heart valve (401), as the implantable heart valve (401) is reversibly coupled with the distal end (411) of the valve delivery catheter (410). Additionally, because the ultrasound imaging catheter is not coupled to the valved delivery catheter (410), the ultrasound imaging catheter (420) moves independently the as the valve delivery catheter (410) and the implantable heart valve (401) (i.e., the ultrasound imaging catheter (420) may remain stationary as the implantable heart valve (401) is positioned and deployed from the valve delivery catheter (410); See FIG. 21B or 19A or 19B).

The image does not show the valve leaflets (e.g., as in FIGS. 1A-1F) for the overall implant that contributes to the inner diameter space constraints or the specific delivery system features that may be employed. Yet, the image illustrates the general hardware (stent frame, delivery system/sheath components and IVUS device) that may be employed in the subject systems and methods.

FIG. 17 is a perspective view of a stent frame 20 component that may be employed therein. Actually, this figure provides an enlarged view of the stent frame shown in FIGS. 7A and 7B. So-enlarged, features in addition to those of the stent in U.S. Pat. No. 8,133,270 upon which the overall architecture may be based are easily highlighted. Specifically, two sets of holes 22 and 24 (proximal and more distal) are provided at the proximal side 32 of the stent frame 20 (i.e., on the "top" of the stent that would be positioned in the aortic root). These holes allow for passage of a network of pull-strings or filaments used for step-wise deployment, repositioning of the stent, and retrievability back to the guide-wire catheter (as discussed above) and also lateral positioning (as discussed below). Further, T-shaped structures 4 at the proximal side 32 are added to proximal crown features 26 to accommodate repositioning and retrievability of the valve during implantation procedure by way of attachment to complimentary delivery system features 40 like the example shown in FIGS. 14A and 14B.

In addition, connector holes 6 in tabs 8 of material at the middle of a number of struts 28 are provided to accommodate locking with pin-shape structures that permanently affix/connect the valve 10 material to the stent frame structure as further described in U.S. patent application Ser. No. 13/773,389 filed Feb. 21, 2013, which application is incorporated by reference herein in its entirety. A set of distal holes 12 at distal end 30 or "bottom" ventricular side of the stent advantageously provide attachment points (e.g., by suturing) of the valve leaflets to the stent frame as illustrated in FIGS. 1A-1F.

FIGS. 18A and 18B are side views of the same stent frame 20 associated with a delivery system 200' related to that in FIGS. 5A-10B, but including additional manipulation features. Specifically, the delivery system 200' is adapted for controlling the lateral position of a heart valve device, for positioning or repositioning during deployment. Draw lines (or filaments) 230 (configured as in the referenced embodiments) are further connected to a pivot fitment 250 and a joystick-type handle 252.

As shown in FIGS. 19A and 19B loops or end ties 236 around spurs 256 may provide such a connection. As likewise shown, fitment 250 (alternatively, a boss, cap or housing) may ride upon or otherwise incorporate one or more spherical bearing surfaces 254/254'.

However configured, operation of system 200' is such that the angular ordering of the draw lines 230 in the overall heart valve (stent frame 20 shown) will correspond to the angular ordering of the draw lines on pivot fitment 250. Such activity is assured by the corresponding relationship of draw lines (or filaments) as shown in cross-sections A-A and B-B in FIG. 18A. The radial orientation of filaments 230 at the stent frame 20 and leading to the stent frame are matched with the radial orientation of the filaments at fitment 250 is indicated by the matching numeral position in the two cross-sectional views.

Therefore, as shown in FIG. 18B, tilting the pivot fitment 250 (e.g., by lever arm/joystick 252) causes coordinated pull and release (or relaxation) of the draw lines proportional to the angular ordering and the direction of tilt to drive a corresponding change in the lateral position of the heart valve device (denoted by the directional arrows). Thus, the lateral position of the heart valve device can be controlled and manipulated by tilting the pivot fitment. While a joystick or similar interface can be pivot fitment. While a joystick or similar interface can be incorporated into or connected to the pivot fitment to facilitate control of the tilt mechanism, other approaches including remote/robotic control are contemplated as well.

In any case, FIGS. 19A and 19B are photographs of a functional prototype 200" of the delivery system embodiment diagrammatically shown in FIGS. 18A and 18B. Here, blocks 260, 262 simulate the end constraint conditions of a catheter body. Between these, filaments 230 are visible (whereas they would generally be housed within a catheter body/sleeve). A short sleeve 264 extends from block 262 to simulate the distal portion of the catheter body 220 shown in FIGS. 5A-10B, 18A and 18B including its side apertures 222 and an end hole 224.

In FIG. 19A, stent frame 20 and pivot fitment 250 are shown in a neutral or "home" position. While being tilted/turned, as shown in FIG. 19B, pivot fitment 250 reorients the filaments 230 to move stent 20 laterally in relation to sleeve 264. FIG. 21B further illustrates the positioning and deployment of the implant (e.g., the implantable heart valve; as shown in FIGS. 19A and 19B) but includes the ultrasound imaging catheter (420) inserted within the delivery system (200 or 100) to further clarify the invention.

Finally, FIG. 20 diagrammatically illustrates an alternative user interface for the FIGS. 18A and 18B delivery system. Here, instead of using a handle, a model 260 of the implant 2 (or at least the stent frame 20) to be delivered is employed. The model may be a scale replica of the stent frame 20 and/or the entire implant 2. Generally, it will be configured in an expanded shape. However, it may be controlled so that its state of expansion matches that of implant 2. Alternatively, manipulation of the model expansion may alter the expansion state of the implant. Given all of these options, however, the model will generally at least serve as an interface for lateral valve positioning.

In which case, the model may be connected to the filaments in the same manner/fashion as the stent frame 20 to be manipulated along a catheter centerline 270 by movement of the model in any combination of lateral directions indicated by the axis arrows shown. Alternatively, model 260 may overlay and be connected to fitment 252 to which the filaments are connected (e.g., at spurs 254).

Use of the model 260 in manipulating the stent frame 20 and being able to visualize the direct correspondence of movement between the implant (via fluoroscopy or other medical imaging) to the sight of the model in hand may be particularly beneficial to a physician in attempting ideal implant positioning and placement. In a method of use, the method may comprise at least partially deploying stent frame 20 by withdrawing a sheath 210 covering the stent frame and relaxing the filaments 230 passing through a catheter sleeve 220 and attached to the stent frame to expand the stent frame (e.g., as in such activity shown in FIGS. 5A-5C). Then, a proximal interface such as a joystick or model is manipulated to move the stent frame laterally relative to the catheter sleeve by selectively tightening and relaxing the filaments (e.g., as in such activity shown in FIG. 18B relative to a zero or neutral position of fitment 252). Naturally, the device can be returned to center and then recompressed and/or resheathed for repositioning as well.

In the various delivery system architectures, the catheter/pusher shaft or sleeve may comprise a simple extrusion (e.g., P IFE, FEP, PEEK, PI etc.) or may be constructed using conventional catheter construction techniques and include a liner, braid support and outer jacket (not shown). Likewise, the various tubular members may comprise extrusion (per above), metal hypotube, etc. Further, the stent frame may be constructed using conventional laser cutting and electropolishing techniques and/or be otherwise constructed. In embodiments intended for tracking through a guide/delivery catheter without an incorporated sheath, a loading sheath (optionally peel-away or splittable) may be provided over the implant. Other typical percutaneous access instruments (such as wires, etc.), valves, and other hardware may also be employed in connection with the subject matter described herein.

The subject methods may include each of the physician activities associated with implant positioning, re-positioning, retrieval and/or release. Regarding these methods, including methods of manufacture and use, these may be carried out in any order of events which is logically possible, as well as any recited order of events.

Furthermore, where a range of values is provided, it is understood that every intervening value, between the upper and lower limit of that range and any other stated or intervening value in the stated range is encompassed within the invention. Also, it is contemplated that any optional feature of the described variations may be set forth and claimed independently, or in combination with any one or more of the features described herein.

Reference to a singular item includes the possibility that there are a plurality of the same items present. More specifically, as used herein and in the appended claims, the singular forms “a,” “an,” “said,” and “the” include plural referents unless specifically stated otherwise. In other words, use of the singular forms allow for “at least one” of the subject item in the description above as well as the claims below. It is further noted that the claims may exclude any optional element and may explicitly limit each element to a “single” instance or “only one” such instance of that element. As such, this paragraph is intended to serve as an antecedent basis for the use of such exclusive terminology as “solely,” “only,” “a single” and the like in connection with the recitation of claim elements, or the use of a negative limitation.

Without the use of such exclusive terminology, the terms “comprising,” “including,” and “having” in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the different embodiments or aspects described herein is not to be limited to the examples provided and/or the subject specification, but rather only by the scope of the issued claim language.

As used herein, the term “about” refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase “comprising” includes embodiments that could be described as “consisting essentially of” or “consisting of”, and as such the written description requirement for claiming one or more embodiments of the present invention using the phrase “consisting essentially of” or “consisting of” is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A delivery system (400) comprising:

an implantable heart valve (401);

a valve delivery catheter (410) comprising a first lumen (415), wherein the valve delivery catheter (410) is reversibly coupled with the implantable heart valve (401) at a distal end (411) of the valve delivery catheter (410), and an ultrasound imaging catheter (420) inserted through the center of the first lumen (415) of the valve delivery catheter (410), wherein the ultrasound imaging catheter (420) comprises a guide wire lumen (425) and an ultrasound imaging transducer (430) located at a distal end (421) of the ultrasound imaging catheter (420) and is configured to advance distally beyond the distal end (411) of the valve delivery catheter to a target site;

wherein the ultrasound imaging catheter (420) is configured to moveably pass:

(i) over a guide wire passing through the guide wire lumen (425) of the ultrasound imaging catheter (420), (ii) through the first lumen (415) of the valve delivery catheter (410), and (iii) through the implantable heart valve (401), and wherein the ultrasound imaging transducer (430) can be moveably positioned to capture images of a surrounding anatomy, the valve delivery catheter (410) and the implantable heart valve (401) in real time during delivery of the implantable heart valve (401) in a subject, wherein the ultrasound imaging transducer (430) remains stationary while the implantable heart valve (401) is pushed forward towards and exits through the distal end (411) of the delivery catheter (410) for deployment.

2. The delivery system of claim 1, wherein the implantable heart valve (401) comprises a self-expandable stent frame.

3. The delivery system of claim 2, wherein the implantable heart valve (401) is a prosthetic aortic valve and the delivery catheter (410) is adapted for transcatheter aortic valve replacement (TAVR) applications.

4. The delivery system of claim 1, wherein the position of the implantable heart valve (401) can be viewed circumferentially and in an axial direction.

5. The delivery system of claim 1, wherein the ultrasound imaging catheter (420) comprises radiopaque shaft markers that are coordinated with corresponding markers on the valve delivery catheter (410).

* * * * *